United States Patent [19]

Enhsen et al.

[11] Patent Number: 5,512,558
[45] Date of Patent: Apr. 30, 1996

[54] NOR-BILE ACID DERIVATIVES, PROCESSES FOR THEIR PREPARATION AND THE USE OF THESE COMPOUNDS AS MEDICAMENTS

[75] Inventors: Alfons Enhsen, Büttelborn; Heiner Glombik, Hofheim; Werner Kramer, Mainz; Günther Wess, Erlensee, all of Germany

[73] Assignee: Hoechst Aktiengesellschaft, Frankfurt am Main, Germany

[21] Appl. No.: 238,514

[22] Filed: May 5, 1994

[30] Foreign Application Priority Data

May 8, 1993 [DE] Germany .................. 43 15 370.4

[51] Int. Cl.$^6$ .................. A61K 31/56; C07J 53/00
[52] U.S. Cl. .................. 514/182; 552/509; 514/179
[58] Field of Search .................. 552/509; 514/182

[56] References Cited

U.S. PATENT DOCUMENTS

| 4,104,285 | 8/1978 | Gallo-Torres et al. ............. 260/397 |
| 5,250,524 | 10/1993 | Kramer et al. ................. 552/509 |

FOREIGN PATENT DOCUMENTS

| 0417725A2 | 3/1991 | European Pat. Off. . |
| 0489423A1 | 6/1992 | European Pat. Off. . |

OTHER PUBLICATIONS

Chemical Abstracts, vol. 113, No. 19, Nov. 5, 1990, Abstract No. 172419, "Synthesis of a new molecular receptor based on cholic acid".

Chemical Abstracts, vol. 116, No. 11, 1992, Abstract No. 103302, "Hepatic and ileal transport and effect on biliary secretion of norursocholic acid and its conjugates in rats".

Chemical Abstracts, vol. 103, No. 17, 1985, Abstract No. 134429, "Intestinal Absorption and Metabolism of Nor-cholic Acid in Rats".

Journal Of Medicinal Chemistry, G. Wess et al., "Specific Inhibitors of Ileal Bile Acid Transport.", vol. 37, No. 7, Apr. 1, 1994.

"Synthesis of 24–nor–5β–cholan–23–oic acid derivatives: a convenient and efficient one–carbon degradation of the side chain of natural bile acids", Schteingart et al., Journal of Lipid Research, 29:1387–1395 (1988).

Primary Examiner—Marianne M. Cintins
Attorney, Agent, or Firm—Finnegan, Henderson, Farabow, Garrett & Dunner

[57] ABSTRACT nor-Bile acid derivatives, processes for their preparation and the use of these compounds as medicaments nor-Bile acid derivatives of the formula I $$G1-X-G2 \qquad I$$

in which G1, G2 and X have the meanings given, processes for the preparation of these compounds and medicaments are described. On the basis of their pharmacological action, they can be used as an antihyperlipidemic agent.

5 Claims, No Drawings 5,512,558

NOR-BILE ACID DERIVATIVES, PROCESSES FOR THEIR PREPARATION AND THE USE OF THESE COMPOUNDS AS MEDICAMENTS

DESCRIPTION nor-Bile acid derivatives, processes for their preparation and the use of these compounds as medicaments The invention relates to bile acid derivatives of the formula I

G1—X—G2    I processes for their preparation, pharmaceutical preparations based on these compounds and the use of the bile acid derivatives as medicaments.

Bile acids have an important physiological function in lipolysis, for example as cofactors of pancreatic lipases and as natural detergents for solubilizing fats and fat-soluble vitamins. As the end product of cholesterol metabolism, they are synthesized in the liver, stored in the gallbladder and secreted from this by contraction into the small intestine, where they display their physiological action. The greatest proportion of bile acids secreted is recovered via the enterohepatic circulation. They return to the liver via the mesenterial veins of the small intestine and the portal vein system. Both active and passive transportation processes play a role in re-absorption in the intestine. The major proportion of the bile acids is resorbed at the end of the small intestine, the terminal ileum, by a specific $Na^+$-dependent transportation system, and passes with the mesenterial venous blood via the portal vein back to the liver, to be secreted again by the liver cells into the bile. The bile acids appear in the enterohepatic circulation both as free acids and in the form of glycine conjugates and taurine conjugates.

Most natural bile acids have a C-24 carboxyl group in free or conjugated form in the side chain on the D-ring of the steroid structure. Bile acids in which the side chain is shortened by one or more carbon atoms, also called nor-bile acids, have a free or conjugated carboxyl group correspondingly on carbon atoms 23, 22 or 20. Some of these compounds occur in traces in natural bile. Nor-bile acids differ from $C_{24}$-bile acids in some metabolic and physiological properties (J. Lip. Res. 29, 1387, 1988).

Non-absorbable, insoluble, basic, crosslinked polymers have been used for a long time for binding bile acids and are utilized therapeutically on the basis of these properties. Bile acid derivatives described in Patent Application EP-A-0 489 423 have a high affinity for the intestinal bile acid transportation system and therefore allow specific inhibition of the enterohepatic circulation. All diseases in which inhibition of bile acid absorption in the intestine, especially in the small intestine, seems desirable are regarded as a therapeutic aim. For example, biligenic diarrhea following ileum resection, or else increased blood cholesterol levels are treated in this manner. In the case of an increased blood cholesterol level, a reduction in this level can be achieved by intervention in the enterohepatic circulation. Reducing the bile acid pool in the enterohepatic circulation forces corresponding new synthesis of bile acids from cholesterol in the liver. The LDL cholesterol in the blood circulation is resorted to in order to meet the cholesterol requirement in the liver, the hepatic LDL receptors increasingly being used. The resulting acceleration in LDL catabolism has the effect of reducing the atherogenic cholesterol content in the blood.

There was the object of discovering novel medicaments which are capable of reducing the atherogenic cholesterol content in the blood and of influencing the enterohepatic circulation in respect of increased bile acid secretion and a resulting reduction in the cholesterol level.

This object is achieved by the bile acid derivatives according to the invention.

The invention therefore relates to bile acid derivatives of the formula I

G1—X—G2    I in which

G1 and G2 are bile acid radicals or modified bile acid radicals, and in which at least one of the bile acid radicals G1 or G2 is shortened by one or more carbon atoms in the side chain and X is a bridge group or a covalent bond, in which G1 and G2 are bonded via X as desired.

Modified bile acid radicals are bile acid radicals in the form of the free acid, the esters or amides, the salt forms, the forms derivatized on the hydroxyl groups and dimeric bile acid radicals, such as are described, for example, in EP-A-0 489 423.

The compounds according to the invention have a high affinity for the specific bile acid transportation system of the small intestine and inhibit bile acid resorption in a concentration-dependent and competitive manner.

Furthermore, the compounds according to the invention are not themselves absorbed, and therefore do not enter into the blood circulation. By applying this action principle, the enterohepatic circulation of the bile acids can be interrupted very specifically and efficiently.

By using the compounds according to the invention, it is possible to reduce the amount of bile acid in the enterohepatic circulation such that a reduction in the cholesterol level of the serum takes place. Avitaminoses are just as unlikely during use as an influence on the absorption of other medicaments or an adverse effect on the intestinal flora. Furthermore, the side effects known from polymers (constipation,, steratorrhea) are not observed, i.e. lipolysis is not adversely influenced. Because of the high affinity for the specific bile acid transportation system of the small intestine, low daily doses are sufficient, so that the acceptance of such medicaments by the doctor and patient will be very high.

Preferred compounds of the formula I are those in which the linkage between the bile acid radicals G1 and G2 is not symmetric, i.e. a particular ring of the steroid structure of G1 is not linked to its corresponding ring of the steroid structure of G2 via X, at least one of the bile acids G1 or G2 being shortened in the side chain by one or more carbon atoms.

Particularly preferred compounds of the formula I are those in which the bile acid radical G1, which is a bile acid or a modified bile acid, is linked to the bonding member X via the side chain on the D-ring, X is a bridge group or a covalent bond and the bile acid radical G2, which is a bile acid or a modified bile acid, is bonded to X via the A-ring, at least one of the bile acid radicals G1 or G2 being shortened in the side chain by one or more carbon atoms.

Especially preferred compounds of the formula I are those in which G1 is a radical of the formula II

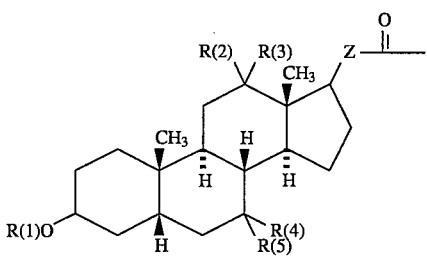

in which

Z is one of the following radicals

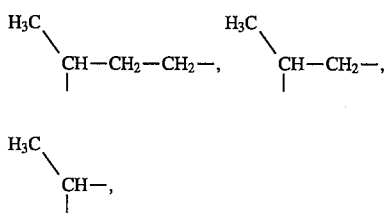

or a single bond,

R(1) is H, an alkyl radical having 1 to 10 carbon atoms, an alkenyl radical having 2 to 10 carbon atoms, a cycloalkyl radical having 3 to 8 carbon atoms, a benzyl radical, which is unsubstituted or mono- to trisubstituted by F, Cl, Br, $(C_1-C_4)$-alkyl or $(C_1-C_4)$-alkoxy, a diphenylmethyl radical, which is unsubstituted or mono- to trisubstituted in one or in both phenyl groups by F, Cl, Br, $(C_2-C_4)$-alkyl or $(C_1-C_4)$-alkoxy, a triphenylmethyl radical, which is unsubstituted or mono- to trisubstituted in one, two or three phenyl radicals by F, Cl, Br, $(C_1-C_4)$-alkyl or $(C_1-C_4)$-alkoxy, or a radical of the formula

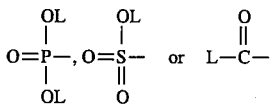

in which L is H, an alkyl radical having 1 to 10 carbon atoms, an alkenyl radical having 2 to 10 carbon atoms, a cycloalkyl radical having 3 to 8 carbon atoms, a phenyl radical, which is unsubstituted or mono- to trisubstituted by F, Cl, Br, $(C_1-C_4)$-alkyl or $(C_1-C_4)$-alkoxy, or a benzyl radical, which is unsubstituted or mono- to trisubstituted by F, Cl, Br, $(C_1-C_4)$-alkyl or $(C_1-C_4)$-alkoxy, R(2)–R(5), where R(2) and R(3) or R(4) and R(5) alternatively in each case together are the oxygen of a carbonyl group, or individually and in each case independently of one another are H, —OL, —SL or —NHL, in which L has the meaning given, X is a single bond or a bridge member of the formula III

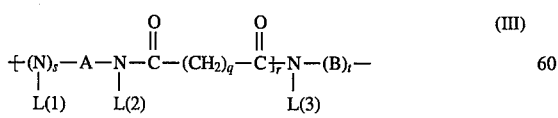

in which

A is an alkylene chain, which is branched or unbranched, it being possible for the chain optionally to be interrupted by —O—, —S— or phenylene, the linkage to the phenyl ring being in the ortho-, meta- or para-position and the chain comprising in total 2 to 12, preferably 2 to 6, chain members p, B is an alkylene chain which is branched or unbranched, it being possible for the chain optionally to be interrupted by —O—, —S— or phenylene, the linkage to the phenyl ring being in the ortho-, meta- or para-position and the chain comprising in total 2 to 12, preferably 2 to 6, chain members n, L(1), L(2) and L(3) are identical or different and have the meaning of L and q is 0 to 5, r is 0 or 1, s is 0 or 1 and t is 0 or 1, and G2 is a radical of the formula IV

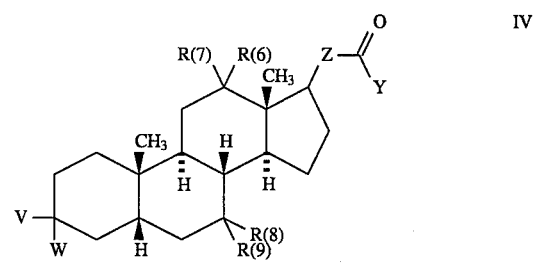

in which Z is one of the following radicals

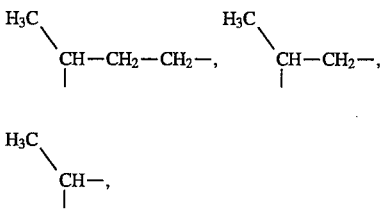

or a single bond,

V is

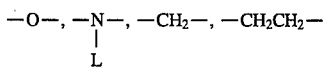

W is H or, if V is —CH$_2$— or —CH$_2$CH$_2$—, is also OH,

Y is

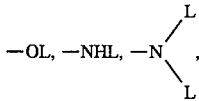

or an amino acid or aminosulfonic acid bonded via the amino group, such as, for example, —NH—CH$_2$—COOH, —NH—CH$_2$—CH$_2$—SO$_3$H,

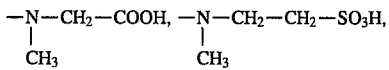

and the $(C_1-C_4)$-alkyl esters and alkali metal and alkaline earth metal salts thereof, or —OKa, in which Ka is a cation, in particular an alkali metal or alkaline earth metal ion, or also a quaternary ammonium ion, and in which L is H, an alkyl radical having 1 to 10 carbon atoms, an alkenyl radical having 2 to 10 carbon atoms, a cycloalkyl radical having 3 to 8 carbon atoms, a phenyl radical, which is unsubstituted or mono- to trisubstituted by F, Cl, Br, $(C_1-C_4)$-alkyl or $(C_1-C_4)$-alkoxy, or a benzyl radical, which is unsubstituted or mono- to trisubstituted by F, Cl, Br, $(C_1-C_4)$-alkyl or $(C_1-C_4)$-alkoxy, and R(6)–R(9), where R(6) and R(7) or R(8) and R(9) alternatively in each case together are the oxygen of a carbonyl group, or individually and in each case independently of one another are H, —OL, —SL or —NHL, in which L has the meaning given, and at least one of the two bile acid radicals G1 or G2 is shortened in the side chain by one or more carbon atoms, i.e. Z is a bond,

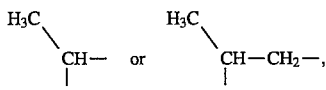

Especially preferred compounds of the formula I are those in which G1 is linked via the side chain on ring D with the bonding member X to ring A of G2, and in which G1 is a radical of the formula II

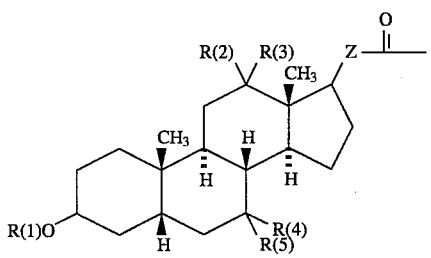

in which

Z is one of the following radicals

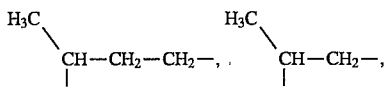

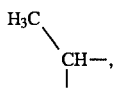

or a single bond,

R(1) is H, an alkyl radical having 1 to 10 carbon atoms or an alkenyl radical having 2 to 10 carbon atoms, R(2) to R(5), where R(2) and R(3) or R(4) and R(5) in each case together are the oxygen of a carbonyl group, or in each case independently of one another are H or OH, X is a single bond or a bridge member of the formula III

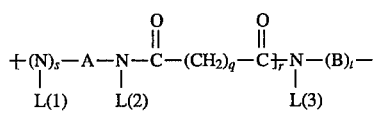

in which

A is an alkylene chain, which is branched or unbranched, and where the chain can optionally be interrupted by —O— or —S— and comprises 2 to 6 chain members p, B is an alkylene chain, which is branched or unbranched, and where the chain can optionally be interrupted by —O— or —S— and comprises 2 to 6 chain members n, L(1), L(2) and L(3) are identical or different and are H, $C_1-C_4$-alkyl or benzyl and q is 0 to 5, r is 0 or 1, s is 0 or 1 and t is 0 or 1, and G2 is a radical of the formula IV

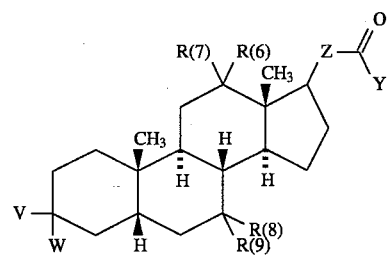

in which Z is one of the following radicals

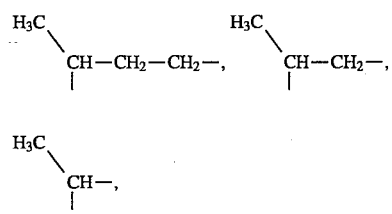

or a single bond,

V is

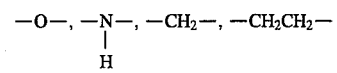

W is H or, if V is —CH$_2$— or —CH$_2$CH$_2$—, is also OH,

Y is

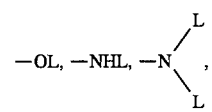

or an amino acid or aminosulfonic acid bonded via the amino group, chosen from the group comprising

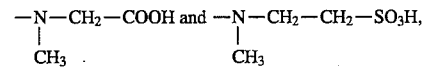

in which L is H, an alkyl radical or alkenyl radical having up to 10 carbon atoms, an alkenyl radical having 2 to 10 carbon atoms, a cycloalkyl radical having 3 to 8 carbon atoms, a phenyl radical, which is unsubstituted or mono- to trisubstituted by F, Cl, Br, $(C_1-C_4)$-alkyl or $(C_1-C_4)$-alkoxy, or a benzyl radical, which is unsubstituted or mono- to trisubstituted by F, Cl, Br, $(C_1-C_4)$-alkyl or $(C_1-C_4)$-alkoxy, and R(6)–R(9), where R(6) and R(7) or R(8) and R(9) in each case together are the oxygen of a carbonyl group, or individually and in each case independently of one another are H or —OH.

Unless stated otherwise, alkyl, alkenyl and alkoxy groups are straight-chain or branched.

The invention furthermore relates to a process for the preparation of compounds of the formula I, which comprises a) in the case of X=a single bond, reacting suitable reactive forms of G1 and G2 with one another by processes which are known in principle, or b) in the case of X=a bridge group, reacting
   α) reactive forms of G1—X with G2 or
   β) reactive forms of G2—X with G1
   with one another by processes which are known in principle.

The processes can be carried out as follows:

a) X=a single bond

The bile acids G1 are employed either in the free form or in protected form. After the linking with G2, which is likewise in free or protected form, if appropriate the protective groups are split off and the carboxyl function is converted into one of the abovementioned derivatives. Suitable protective groups for the alcohol groups are expediently formyl, acetyl, tetrahydropyranyl or t-butyldimethylsilyl. Possible protective groups for the carboxyl group of the side chain are various alkyl or benzyl esters, and also, for example, ortho-esters.

For example, bile acid preferentially reacts in position 3, but also in position 7, with activated forms of carboxylic acids, such as acid chlorides or mixed anhydrides, with addition of bases, such as trialkylamine or pyridine, but also NaOH, at room temperature in suitable solvents, such as tetrahydrofuran, methylene chloride or ethyl acetate, or also dimethylformamide (DMF) or dimethoxyethane (DME).

The various isomers can be separated, for example, by chromatography.

The reaction can be carried out selectively by using suitable protective groups.

Corresponding amino-bile acids can be converted into corresponding amides analogously. Here also, the reaction can be carried out with either protected or free bile acids.

Other compounds according to the invention can be linked analogously by known standard processes.

b) X=a bridge group

The processes described under a) are also used to carry out the linkage of G1—X with G2 or G1 with X—G2.

Here also, the bile acid portion is expediently employed in either protected or unprotected form. A preferred preparation process comprises reacting reactive forms of G1 with reactive forms X—G2. If appropriate, the linkage is followed by splitting off protective groups and converting of the carboxyl group into derivatives.

The preparation of reactive bile acid units is described in the following equations (1 to 4) by the example of cholic acid derivatives (equations 1 and 2 relate to the shortening of the side chain, equations 3 and 4 relate to activation in the 3-position).

Equation 1:

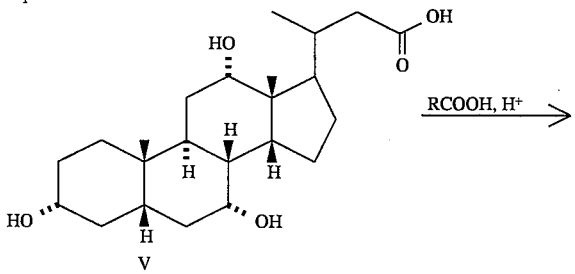

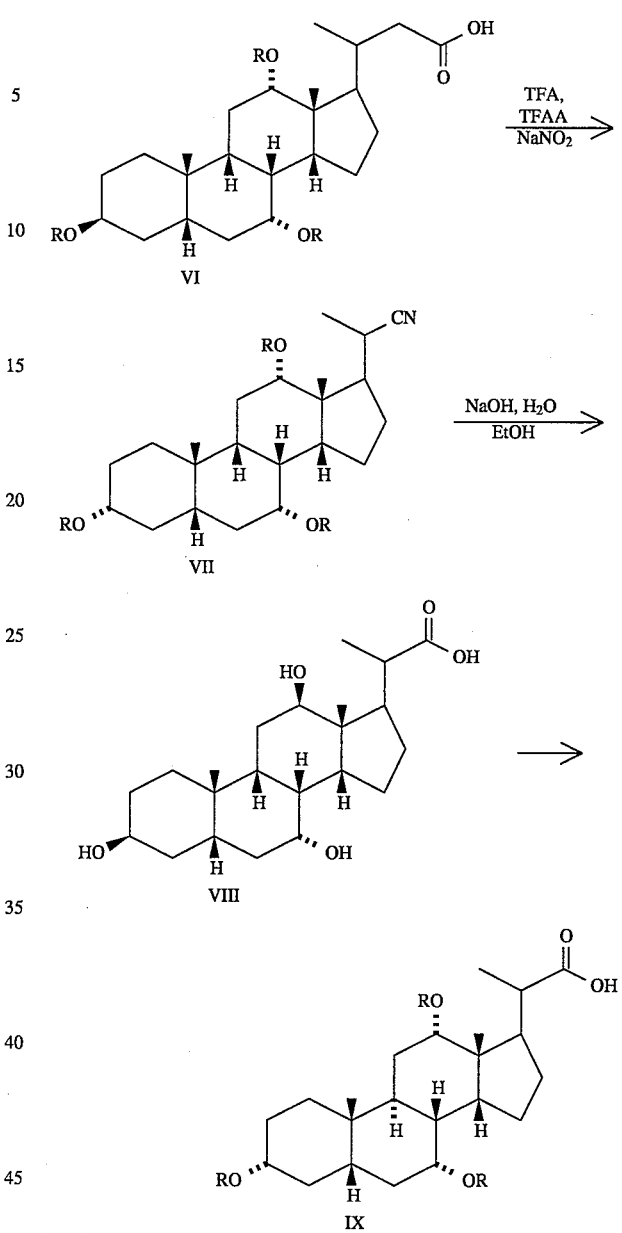

R = Formyl, Acetyl, Benzoyl

The synthesis of nor-cholic acid V from cholic acid has been described by Hofmann et al. (J. Lip. Res. 29, (1988), 1287). In this process, the side chain can also be shortened further to the C-22 carboxylic acid VIII or IX. The hydroxyl groups of the nor-bile acid V are protected, for example by formyl, acetyl or benzoyl protective groups (R). Reaction of the compound VI with trifluoroacetic acid/trifluoroacetic anhydride/sodium nitrite gives the nitrile VII which, by hydrolysis with a strong base, leads to the free bile acid VIII shortened by a further carbon atom. This compound can be employed for further reaction in the unprotected form or in the re-protected form IX (in which R can also be acyl, silyl or tetrahydropyranyl (THP) protective groups).

Equation 2:

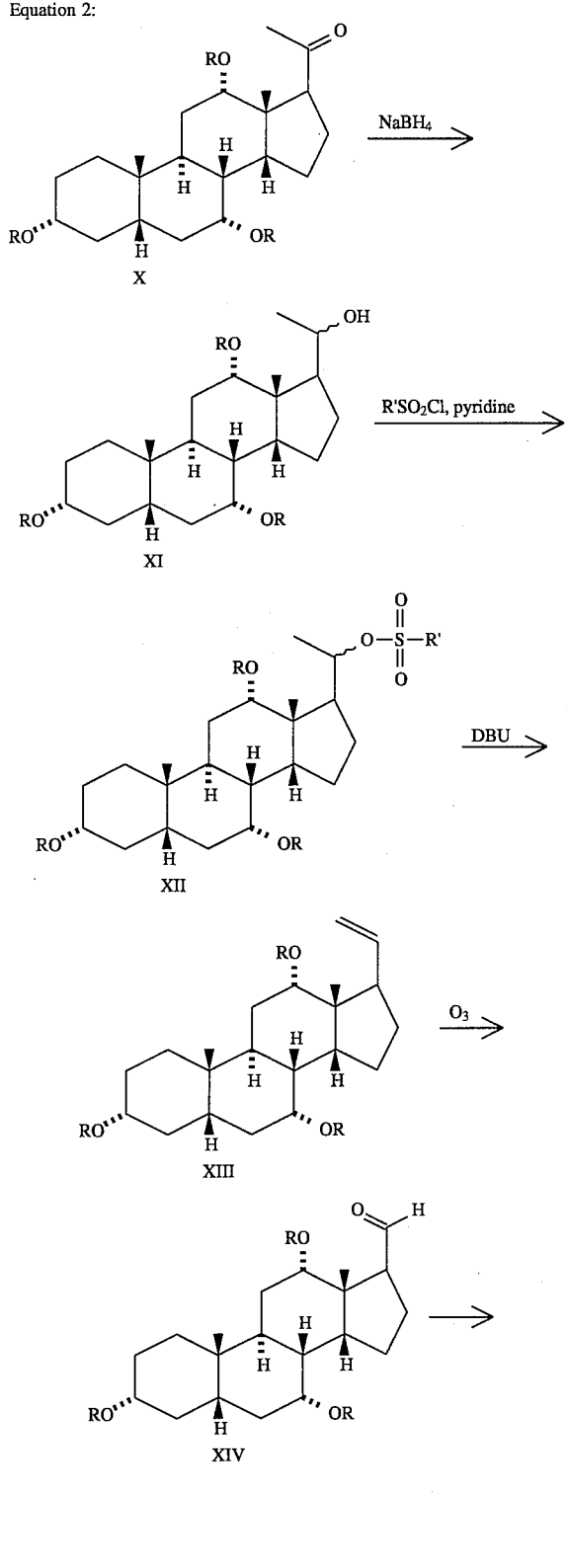

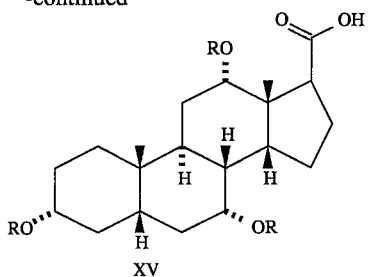

The compound X is reduced to the alcohol XI with sodium borohydride. The alcohol function is activated, for example by a methanesulfonyl or trifluoromethanesulfonyl radical, as in compound XII, and an elimination reaction is subsequently carried out with a suitable base, for example diazabicycloundecene, to give the vinylic system XIII. The 20,21 double bond is split with osmium tetroxide/sodium-periodate or ozone in a suitable solvent to give the aldehyde XIV. Oxidation of XIV by known methods, for example with sodium chloride, leads to the corresponding C-20-carboxyl-bile acid derivative XV.

Equation 3:

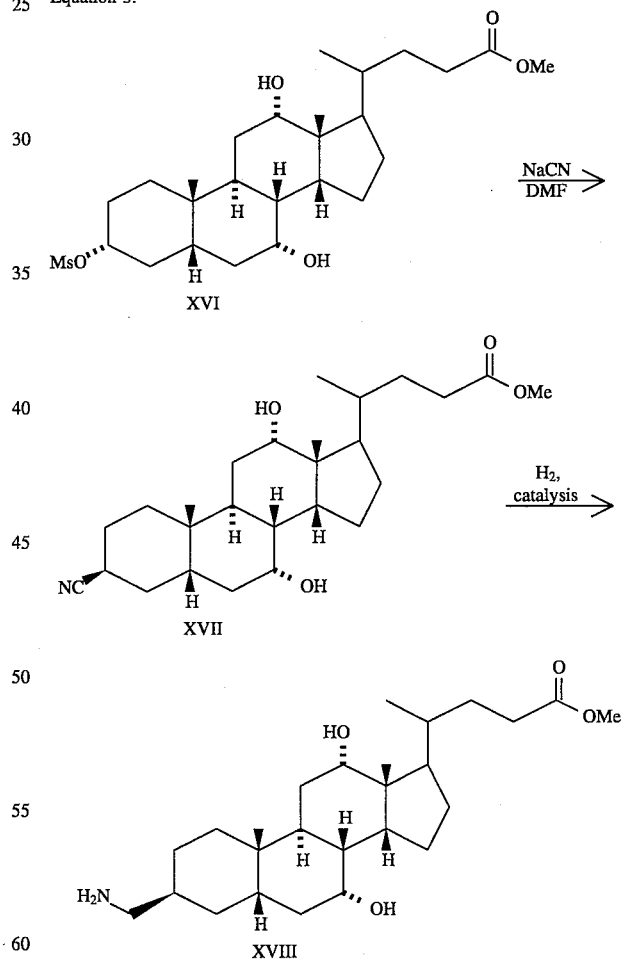

After activation of the 3-hydroxyl function, for example by a methanesulfonyl group, as in compound XVI, a nitrile group can be introduced by nucleophilic substitution with sodium cyanide in a suitable solvent at elevated temperature. The compound XVII thus obtained can be converted into the aminomethyl unit XVIII by hydrogenation with hydrogen in the presence of a suitable catalyst, for example rhodium/$Al_2O_3$.

Equation 4:

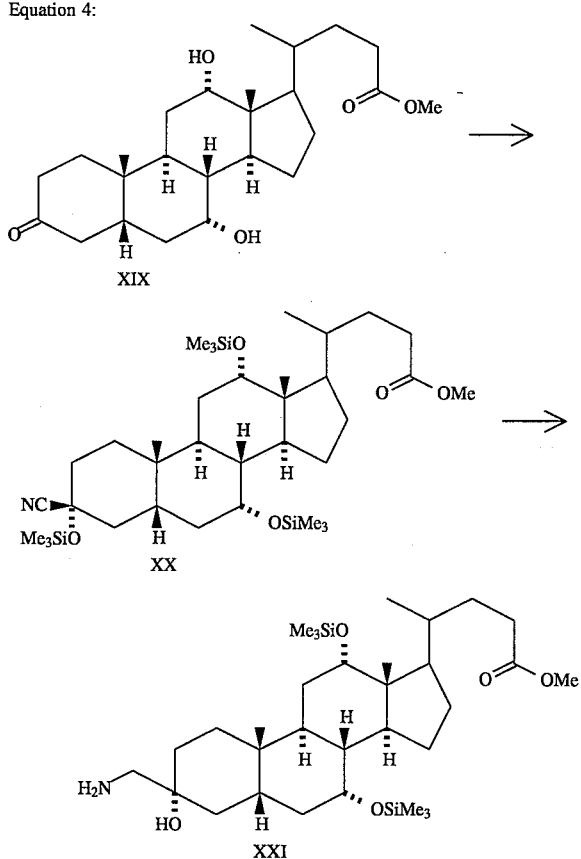

Trimethylsilyl cyanide can be added to 3-ketocholanic acid ester XIX in good yields. Under the reaction conditions chosen (TMSCN, $ZnI_2$, $CH_2Cl_2$), a nitrile derivative XX in which all the hydroxyl groups are silylated is obtained. The nitrile group is directed into the axial β-position by the bulkiness of the TMS group, and the diastereoselectivity is >9:1 (Lit.: Evans et al., J. Org. Chem. 39 (1974) 914). The nitrile function can be reduced to the 3β-aminomethyl derivative XXI with sodium borohydride/trifluoroacetic acid in THF. Cholanic acid derivatives in which the original 3α-hydroxyl functional group is retained, in addition to an additional linker (X), are obtained in this manner.

The invention furthermore relates to the use of the compounds according to the invention for the preparation of a medicine.

For this, the compounds of the formula I are dissolved or suspended in pharmacologically acceptable organic solvents, such as mono- or polyhydric alcohols, such as, for example, ethanol or glycerol, or in triacetin, oils, such as, for example, sunflower oil or cod-liver oil, ethers, such as, for example, diethylene glycol dimethyl ether, or also polyethers, such as, for example, polyethylene glycol, or also in the presence of other pharmacologically acceptable polymeric carriers, such as, for example, polyvinylpyrrolidone, or other pharmaceutically acceptable additives, such as starch, cyclodextrin or polysaccharides. The compounds according to the invention furthermore can be administered in combination with other medicaments.

The compounds of the formula I are administered in various dosage forms, preferably orally in the form of tablets, capsules or liquids. The daily dose varies in the range from 3 mg to 5000 mg, but preferably in the dose range of 10 to 1000 mg, depending on the body weight and constitution of the patient.

On the basis of their pharmacological properties, the compounds are particularly suitable as hypolipidemic agents.

The invention therefore also relates to medicaments based on the compounds of the formula (I) and to the use of the compounds as medicaments, in particular for reducing the cholesterol level.

The compounds according to the invention were tested biologically by determination of the inhibition of [$^3$H]-taurocholate uptake in the brush border membrane vesicle of the ileum of rabbits. The inhibition test was carried out as follows:

1. Preparation of brush border membrane vesicles from the ileum of rabbits

Brush border membrane vesicles were prepared from the intestinal cells of the small intestine by the so-called $Mg^{2+}$ precipitation method. Male New Zealand rabbits (2 to 2.5 kg body weight) were sacrificed by intravenous injection of 0.5 ml of an aqueous solution of 2.5 mg of tetracaine HCl, 100 T 61$^R$ and 25 mg of mebezonium iodide. The small intestine was removed and rinsed with ice-cold physiological saline solution. The terminal 7/10 of the small intestine (measured in the oral-rectal direction, i.e. the terminal ileum, which contains the active $Na^+$-dependent bile acid transportation system) was used for preparation of the brush border membrane vesicles. The intestines were frozen in plastic bags under nitrogen at −80° C. For preparation of the membrane vesicles, the frozen intestines were thawed at 30° C. in a water-bath. The mucosa was scraped off and suspended in 60 ml of ice-cold 12 mMTris/HCl buffer (pH 7.1)/300 mM mannitol, 5 mM EGTA/10 mg/l of phenylmethyl-sulfonyl fluoride/1 mg/l of trypsin inhibitor from soybean (32 U/mg)/ 0.5 mg/l of trypsin inhibitor from bovine lung (193 U/mg)/5 mg/l bacitracin. After dilution to 300 ml with ice-cold distilled water, the mixture was homogenized with an Ultraturrax (18-rod, IKA Werk Stuafen, FRG) for 3 minutes at 75% of the maximum power, while cooling with ice. After addition of 3 ml of 1M $MgCl_2$ solution (final concentration 10 mM), the mixture was left to stand for exactly 1 minute at 0° C. By addition of $Mg^{2+}$, the cell membranes aggregate and precipitate, with the exception of the brush border membranes. After centrifugation at 3000×g (5000 rpm, SS-34 rotor) for 15 minutes, the precipitate is discarded and the supernatant, which contains the brush border membranes, is centrifuged at 267,000×g (15,000 rpm, SS-34 rotor) for 30 minutes. The supernatant was discarded and the precipitate was rehomogenized in 60 ml of 12 mMTris/HCl buffer (pH 7.1)/60 mM mannitol, 5 mM EGTA using a Potter Elvejhem homogenizer (Braun, Melsungen, 900 rpm, 10 strokes). After addition of 0.1 ml of 1M $MgCl_2$ solution and an incubation time of 15 minutes at 0° C., the mixture was centrifuged again at 3000×g for 15 minutes. The supernatant was then centrifuged again at 46,000×g (15,000 rpm, SS-34 rotor) for 30 minutes. The precipitate was taken up in 30 ml of 10 mM Tris/Hepes buffer (pH 7.4)/300 mM mannitol and resuspended homogeneously by 20 strokes in a Potter Elvejhem homogenizer at 1000 rpm. After centrifugation at 48,000×g (20,000 rpm, SS-34 rotor) for 30 minutes, the precipitate was taken up in 0.5 to 2 ml of Tris/Hepes buffer (pH 7.4)/280 mM mannitol (final concentration 20 mg/ml) and resuspended with the aid of a tuberculin syringe with a 27 gauge needle. The vesicles were either used for transportation studies immediately after preparation, or stored at −196° C. in 4 mg portions in liquid nitrogen.

2. Inhibition of the Na$^+$-dependent [$^3$H]-taurocholate uptake in brush border membrane vesicles of the ileum The uptake of substrates in the brush border membrane vesicles described above was determined by means of the so-called membrane filtration technique. 10 μl of the vesicle suspension (100 μg of protein) were pipetted as drops onto the wall of a polystyrene incubation tube (11×70 mm) which contained the incubation medium with the corresponding ligands (90 μl). The incubation medium contained 0.75 μl=0.75 μCi [$^3$H(G)]-taurocholate (specific activity: 2.1 Ci/mmol)/0.5 μl of 10 mM taurocholate/ 8.75 μl of sodium transportation buffer (10 mM of Tris/Hepes, (pH 7.4)/100 mM of mannitol/100 mM of NaCl) (Na—T—B) or 8.75 μl of potassium transportation buffer (10 mM Tris/Hepes (pH 7.4)/100 mM mannitol/100 mM KCl) (K—T—B) and 80 μl of the inhibitor solution in question, dissolved in Na—T buffer or K—T buffer, depending on the experiment. The incubation medium was filtered through a polyvinylidene fluoride membrane filter (SYHV LO 4NS, 0.45 μm, 4 mm φ, Millipore, Eschborn, FRG). The transportation measurement was started by mixing the vesicles with the incubation medium. The concentration of taurocholate in the incubation batch was 50 μM. After the desired incubation time (usually 1 minute), the transportation was stopped by addition of 1 ml of ice-cold stopping solution (10 mMTris/Hepes (pH 7.4)/ 150 mM KCl). The resulting mixture was immediately filtered with suction over a membrane filter of cellulose nitrate (ME 25, 0.45 μm, 25 mm diameter, Schleicher & Schuell, Dassell, FRG) under a vacuum of 25 to 35 mbar. The filter was rinsed with 5 ml of ice-cold stopping solution.

To measure the uptake of the radioactively labeled taurocholate, the membrane filter was dissolved with 4 ml of the scintillator Quickszint 361 (Zinsser Analytik GmbH, Frankfurt, FRG) and the radioactivity was measured by liquid scintillation measurement in a TriCarb 2500 measuring instrument (Canberra Packard GmbH, Frankfurt, FRG). After calibration of the instrument with the aid of standard samples and correction for any chemiluminescence present, the values measured were obtained as dpm (decompositions per minute).

The control values were in each case determined in Na—T—B and K—T—B. The difference in the uptake in Na—T—B and K—T—B gave the Na$^+$-dependent transportation content. The concentration of inhibitor at which the Na$^+$-dependent transportation content was inhibited by 50%—based on the control—was designated the IC$_{50}$ Na$^+$.

The pharmacological data comprise a test series in which the interaction of the compounds according to the invention with the intestinal bile acid transportation system in the terminal small intestine was investigated. The results are summarized in Table 11.

EXAMPLE 1

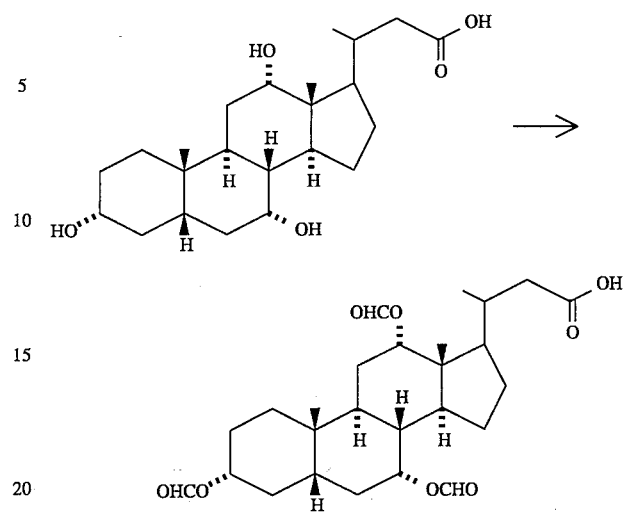

48 g (122 mmol) of 3α,7α,12α-trihydroxy-24-nor-23-cholanic acid (=norcholic acid), 200 ml of formic acid and 1 ml of perchloric acid (60%) are stirred at 50° C. for 1.5 hours, the mixture is cooled to room temperature, 160 ml of acetic anhydride are added and the mixture is stirred for a further 15 minutes. It is poured onto 1.5 l of water and the solid constituents are filtered off with suction and washed with 1 l of water. The residue is dissolved in 700 ml of ether and washed three times with water. The organic phase is dried (MgSO$_4$) and concentrated. Yield 52 g (89%) of Example 1.

MS (FAB, 3-NBA/LiCl) C$_{26}$H$_{38}$O$_8$(478), 485 (M+Li$^+$)

EXAMPLE 2

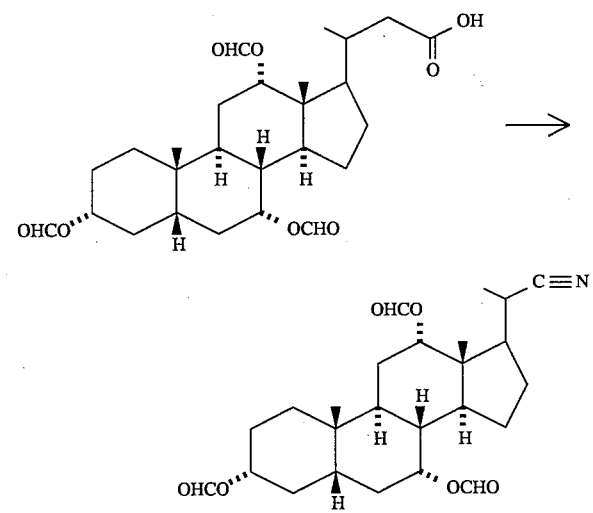

5 g (10.4 mmol) of Example 1 are dissolved in 20 ml of trifluoroacetic acid/5 ml of trifluoroacetic anhydride at 0° C. 840 mg (12 mmol) of sodium nitrite are added in portions in the course of one hour. The mixture is subsequently stirred at 0° C. for a further hour then at 40° C. for 2 hours. The solution is cooled to 0° C. again, neutralized with 5N NaOH and extracted with dichloromethane. The organic phase is dried (MgSO$_4$) and concentrated. Chromatography of the residue over silica gel (cyclohexane/ethyl acetate=2:1) gives 3.1 g (67%) of Example 2.

MS (FAB, 3-NBA/LiCl) $C_{25}H_{35}NO_6$ (445), 452 (M+Li$^+$)

EXAMPLE 3

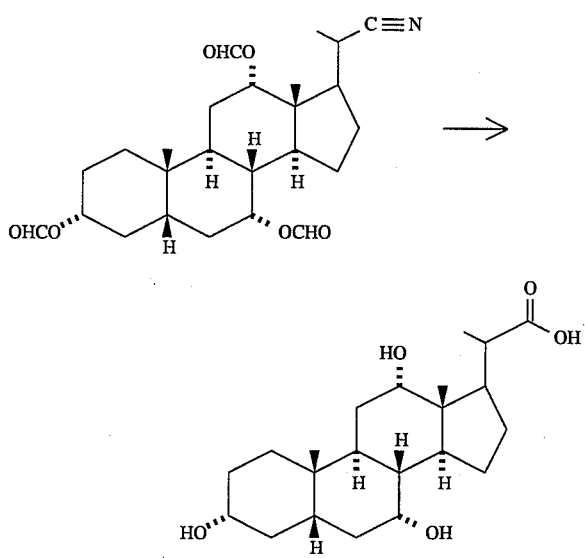

1.5 g (3.37 mmol) of Example 2 and 5 g of KOH are dissolved in 50 ml of ethanol/water (=1:1) and the solution is heated under reflux. When the reaction has ended (monitoring by thin layer chromatography), the ethanol is stripped off and the residue is washed with ether. The aqueous phase is acidified with 2N HCl and extracted three times with ethyl acetate. The combined organic phases are dried (MgSO$_4$) and concentrated. 1.25 g (97%) of Example 3 are obtained.

MS (FAB, 3-NBA/LiCl) $C_{22}H_{36}O_5$ (380), 387 (M+Li$^+$)

EXAMPLE 4

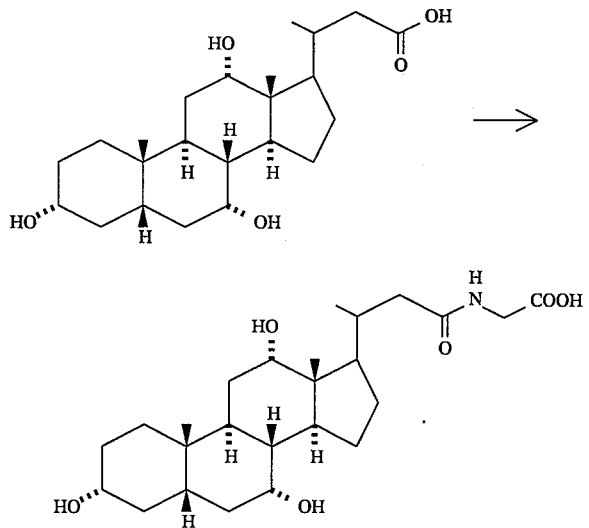

500 mg (12.87 mmol) of 3α,7α,12α-trihydroxy-24-nor-23-cholanic acid and 370 mg (36 mmol) of N-methylmorpholine are dissolved in 20 ml of THF. 0.34 ml (36 mmol) of ethyl chloroformate is added at 10° C. After 15 minutes, a solution of 270 mg (36 mmol) of glycine in 5 ml of 1N NaOH is added dropwise. The mixture is subsequently stirred at room temperature for 18 hours. The reaction mixture is concentrated and the residue is chromatographed over silica gel (dichloromethane/methanol= 8:2). 320 mg (56%) of Example 4 are obtained.

MS (FAB/3-NBA) $C_{25}H_{41}NO_6$ (451), 452 (M+H$^+$)

EXAMPLE 5

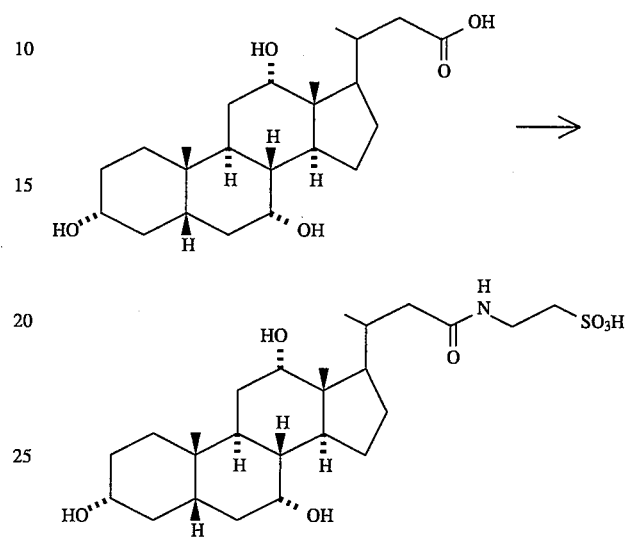

340 mg (53%) of Example 5 are obtained from 500 mg (12.67 mmol) of norcholic acid and 450 mg (836 mmol) of taurine by the process described for Example 4.

MS (FAB, 3-NBA) $C_{25}H_{43}NO_7S$ (501), 502 (M+H$^+$)

EXAMPLE 6

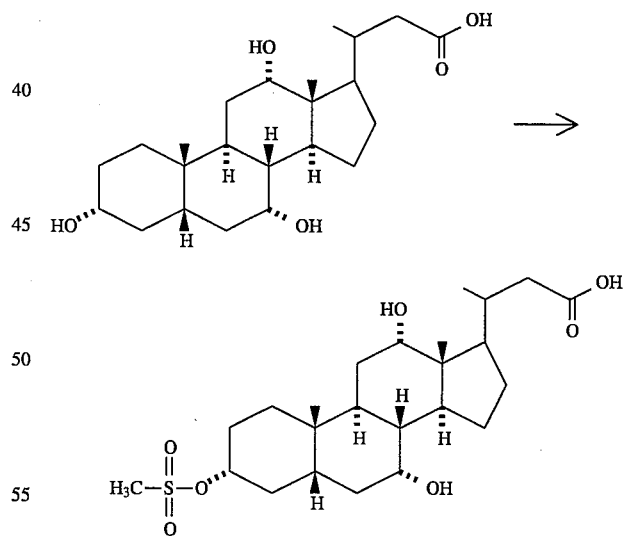

10 g (25.3 mmol) of norcholic acid are dissolved in 50 ml of pyridine. 2.6 ml of methanesulfonyl chloride are added dropwise at 0° C. The reaction mixture is then stirred at room temperature for 3 hours. It is poured onto ice-water and extracted three times with ethyl acetate. The organic phase is dried (MgSO$_4$) and concentrated. The crude product is crystallized from diisopropyl ether, filtered off with suction and then dried in vacuo. 11.2 g (93%) of Example 6 are obtained.

MS (FAB, 3-NBA/LiCl) $C_{24}H_{40}O_7S$ (472), 485 (M+2Li$^+$ −H$^+$)

EXAMPLE 7

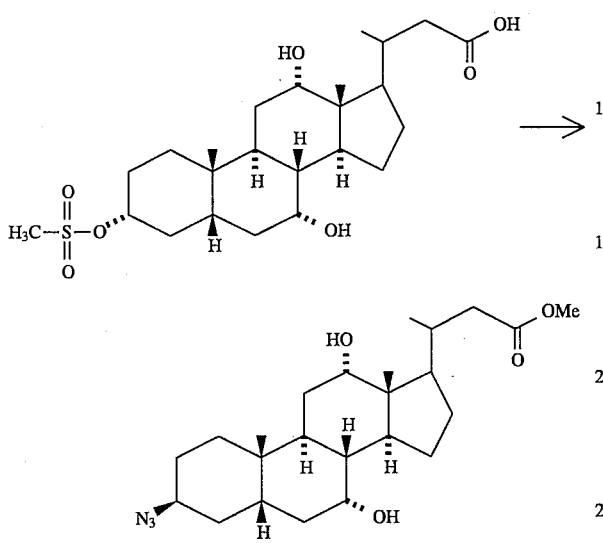

38.7 g (81.9 mmol) of Example 6 and 6.9 g (106 mmol) of sodium azide are stirred in 350 ml of dimethylformamide at 130° C. for 2.5 hours. After cooling, the mixture is poured onto 1.5 l of ice-water and extracted three times with ethyl acetate. The organic phase is dried (MgSO$_4$) and concentrated. The crude product is esterified in a methanolic hydrochloric acid solution, prepared from 100 ml of methanol and 14 ml of acetyl chloride, at room temperature for 2 hours. For working up, the mixture is partly concentrated and the product is poured onto 1 l of water and extracted three times with ethyl acetate. After drying and concentration of the organic phase, the crude product is chromatographed over silica gel (cyclohexane/ethyl acetate=6:4). 9.0 g (25%) of Example 7 are obtained.

MS (FAB, 3-NBA/LiCl) $C_{24}H_{39}N_3O_4$ (433), 440 (M+Li$^+$)

EXAMPLE 8

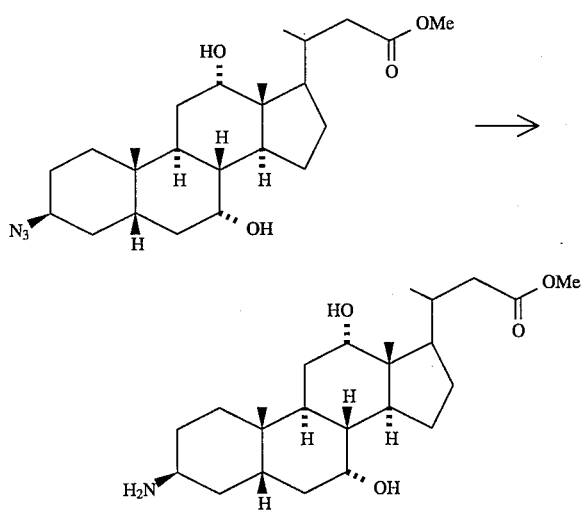

8.0 g (18.5 mmol) of Example 7 are hydrogenated with hydrogen in 220 ml of ethyl acetate in the presence of about 50 mg of 10% Pd/C. When the reaction has ended, the catalyst is filtered off and the filtrate is concentrated. Chromatography of the residue (methanol/triethylamine= 95:5) gives 6.0 g (80%) of Example 8.

MS (FAB, 3-NBA/LiCl) $C_{24}H_{41}NO_4$ (407), 414 (M+Li$^+$)

EXAMPLE 9

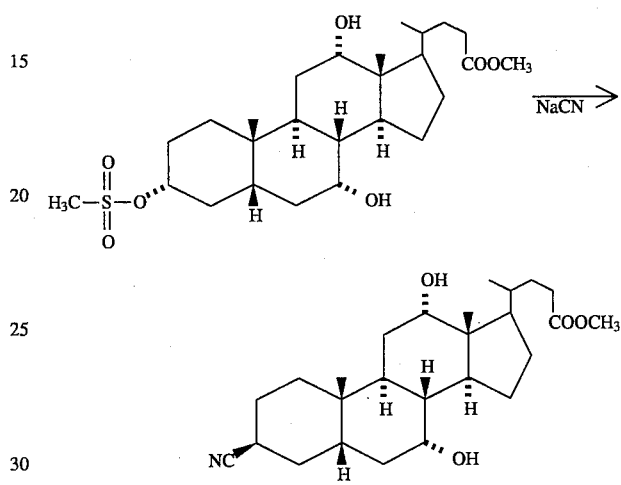

4.3 g (8.6 mmol) of the mesylate (cf. EP-A-0 489 423) are heated at 100 to 110° C. in 80 ml of dry DMF with 0.42 g (8.6 mmol) of sodium cyanide for 3 hours. The mixture is poured onto ice-water and extracted with ethyl acetate, and the residue from the organic phase is filtered over silica gel. (Ethyl acetate/heptane=2:1). 890 mg (25%) of nitrile are obtained.

MS (FAB, 3-NBA/LiCl) $C_{26}H_{41}NO_4$ (431), 438 (M+Li$^+$)

EXAMPLE 10

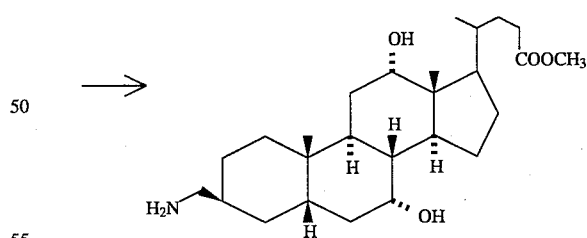

1.5 g (3.48 mmol) of the nitrile from Example 9 are hydrogenated in 100 ml of methanol with addition of 10 ml of concentrated ammonia solution and 1 g of 5% strength rhodium-on-Al$_2$O$_3$ under 140 bar at 50° C. for 24 hours. The catalyst is filtered off with suction, the filtrate is concentrated and the residue is purified over silica gel (CH$_2$Cl$_2$/MeOH/ concentrated NH$_3$ solution=100:15:2). 1.1 g (73%) of amine (Example 10) are obtained.

MS (FAB, 3-NBA/LiCl) $C_{26}H_{45}NO_4$ (435), 442 (M+Li$^+$)

EXAMPLE 11A

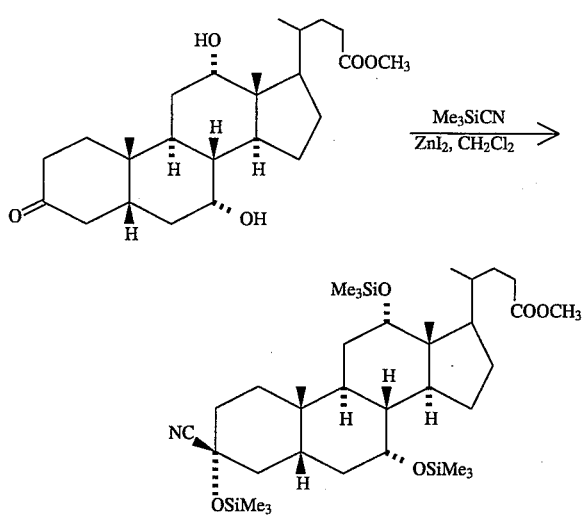

270 mg of dry zinc iodide are added to 9 g (21.4 mmol) of ketone (see equation 4) under argon in 50 ml of dry dichloromethane, and 10 ml (3.5 equivalents) of trimethylsilyl cyanide are added in portions, while cooling with ice. After about 1.5 hours, the reaction has ended. The residue which remains after concentration is purified with n-heptane/ethyl acetate=10:1 over silica gel. 12.1 g (85%) of the product are obtained as a colorless oil which predominantly (>9:1) comprises one stereoisomer.

MS (FAB, 3-NBA/LiCl) $C_{35}H_{65}NO_5Si_3$ (664), 671 (M+Li$^+$)

EXAMPLE 11B

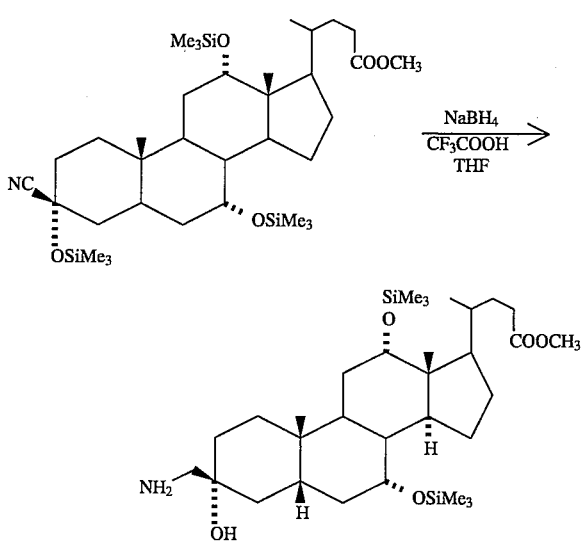

2.1 ml (27.4 mmol) of trifluoroacetic acid are first added to a suspension of 1.036 g (827.4 mmol) of sodium borohydride in dry THF, the mixture is stirred for 15 minutes and 12.1 g (18.2 mmol) of the nitrile from Example 11A in 40 ml of dry THF are then added, while cooling with ice. After 24 hours at room temperature, the mixture is worked up by addition of water and ether, the organic phase is extracted by shaking with hydrogen-carbonate solution and the residue is purified by chromatography with CH$_2$Cl$_2$/CH$_3$OH/concentrated NH$_3$ solution=100:10:1.5. 7.83 g (48%) of the amine are obtained.

MS (FAB, 3-NBA/LiCl) $C_{32}H_{61}NO_5Si_2$ (596), 603 (M+Li$^+$)

EXAMPLE 12A

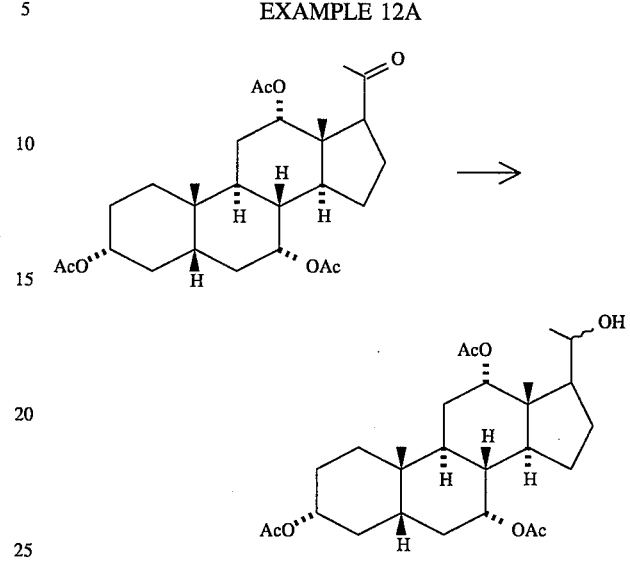

20 g (42 mmol) of methyl ketone (cf. equation 2) are dissolved in 400 ml of methanol, 2.48 g (64 mmol) of sodium borohydride are added and the mixture is stirred at room temperature for 45 minutes. After addition of 400 ml of water, 2N HCl is carefully added until the pH reaches 3. The mixture is concentrated, water is added again and the mixture is extracted with EA. The organic phase is dried and concentrated, and the residue is chromatographed over silica gel (cyclohexane/ethyl acetate 1:1).

Yield: 15.1 g (75%)

MS (FAB, 3-NBA/LiCl) $C_{27}H_{42}O_7$ (478), 485 (M+Li$^+$)

EXAMPLE 12B

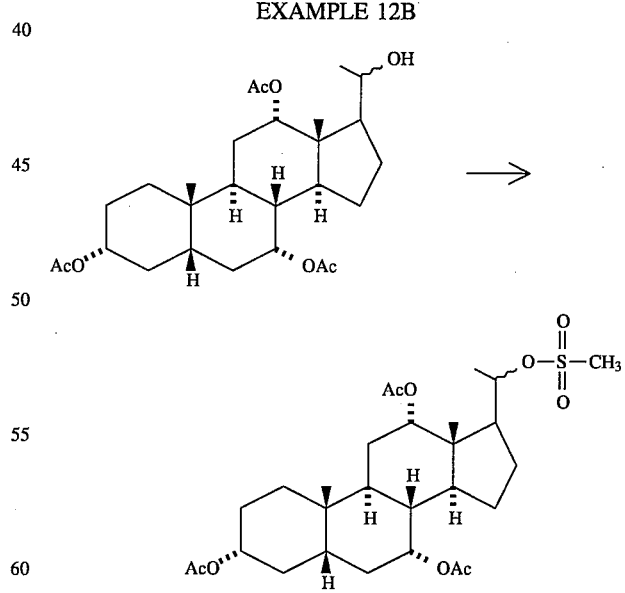

15.1 g (31.5 mol) of alcohol (Example 12A) are dissolved in 250 ml of dichloromethane/250 ml of pyridine, 4 g (35 mmol) of methanesulfonyl chloride are added at 0° C. and the mixture is stirred at room temperature for 2 hours. For working up, water is added and the mixture is extracted with ethyl acetate. After drying and concentration of the ethyl acetate phase, 17.5 g of (quaternary) mesyl compound, which can be reacted without further purification, are obtained.

MS (FAB, 3-NBA/LiCl) $C_{28}H_{44}O_9S$ (556), 563 (M+Li$^+$)

EXAMPLE 12C

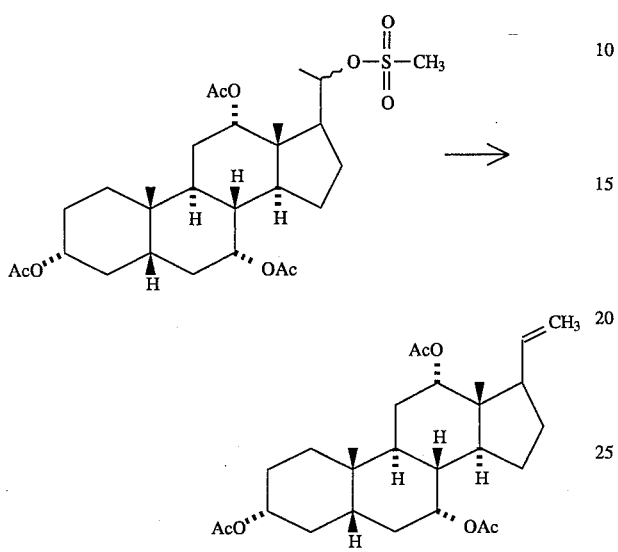

18 g (32.3 mmol) of Example 12B and 80 ml of diazabicycloundecene are dissolved in 400 ml of DMF. The mixture is stirred at 100° C. for 16 hours. After cooling, the reaction mixture is concentrated and the residue is chromatographed over silica gel (cyclohexane/ethyl acetate=7:3). The yield is 9.6 g (64%).

MS (FAB, 3-NBA/LiCl) $C_{27}H_{40}O_6$ (460), 467 (M+Li$^+$)

EXAMPLE 12D

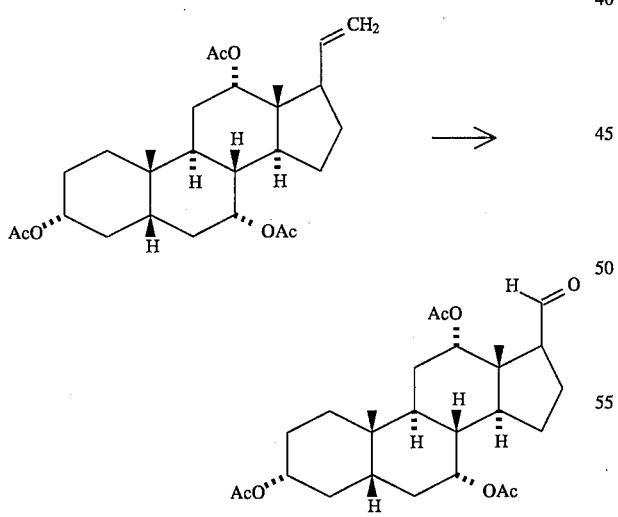

13 g (28.2 mmol) of Example 12C are dissolved in 100 ml of dichloromethane, 10 ml of pyridine are added and the mixture is cooled to −60° C. Ozone is passed in, while stirring, until a blue coloration is obtained. The mixture is then flushed with $N_2$ and warmed to room temperature, and dimethyl sulfide is added. The reaction mixture is concentrated and the residue is chromatographed over silica gel (cyclohexane/ethyl acetate=7.3). 5.8 g (44%) of aldehyde are obtained.

MS (FAB, 3-NBA/LiCl) $C_{26}H_{38}O_7$ (462), 469 (M+Li$^+$)

EXAMPLE 12E

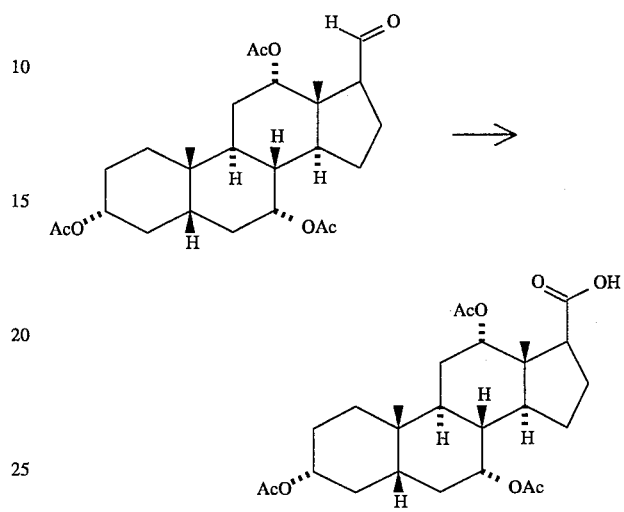

The aldehyde Example 12D is oxidized to the free C-20-carboxylic acid Example 12E by Jones oxidation (J. Chem. Soc. 1953, 2548).

MS (FAB, 3-NBA/LiCl) $C_{26}H_{38}O_8$ (478), 485 (M+Li$^+$)

EXAMPLE 12F

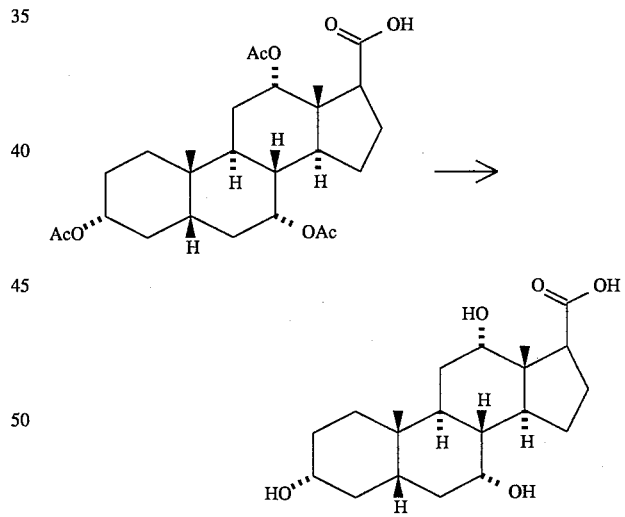

550 mg (1.15 mmol) of Example 12E are dissolved in 20 ml of ethanol, 10 ml of 2N NaOH are added and the mixture is stirred at room temperature for 24 hours. Water is added and the organic solvents are stripped off. The pH is brought to 3 to 4 with 2N HCl. Thereafter, the mixture is concentrated completely and the residue is chromatographed over silica gel (CHCl$_3$/MeOH=4:1). 270 mg (67%) of product are obtained.

MS (FAB, 3-NBA/LiCl) $C_{20}H_{32}O_5$ (352), 359 (M+Li$^+$)

EXAMPLE 13

23      24

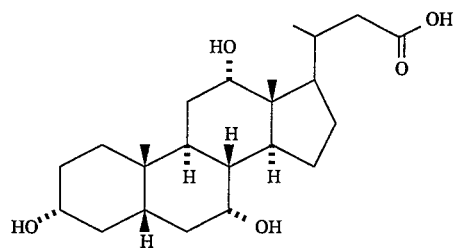 + 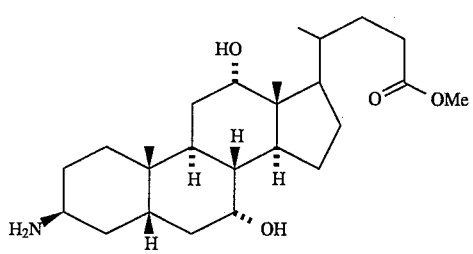 →

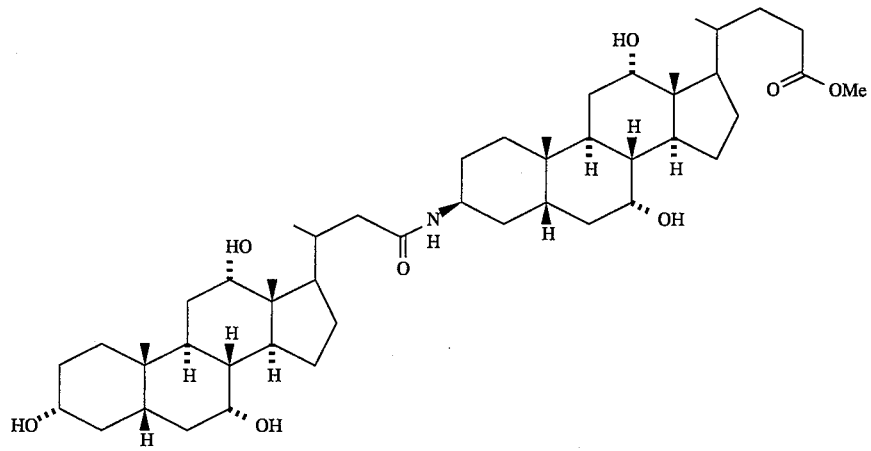

2.0 g (5.01 mmol) of 3α,7α,12α-trihydroxy-24-nor-23-cholanic acid, 2.1 g (4.98 mmol) of methyl 3β-amino-7α,12α-dihydroxy-24-cholanate (cf. EP-A-0 417 725), 1.36 g (10 mmol) of hydroxybenzotriazole and 1.04 g (5.4 mmol) of dicyclohexylcarbodiimide are stirred in 100 ml of dry tetrahydrofuran at room temperature for 24 hours. The reaction mixture is concentrated and the residue is chromatographed over silica gel (chloroform/methanol=85:15). 3.0 g (75%) of Example 13 are obtained.

MS (FAB, 3-NBA/LiCl) $C_{48}H_{79}NO_8$ (798), 805 (M+Li$^+$)

Examples 14 to 31 of Tables 1 to 3 are obtained analogously to Example 13 (reactive —X—G2 derivatives are described in EP-A-0 489 423 or EP-A-0 417 725).

TABLE 1

| Ex. | —X—G2 | MS (FAB, 3-NBA/LiCl) |
|---|---|---|
| 14 | —HN–CH₂CH₂–O–[steroid structure] | $C_{50}H_{83}NO_9$ (842), 849 (M+Li$^+$) |

TABLE 1-continued
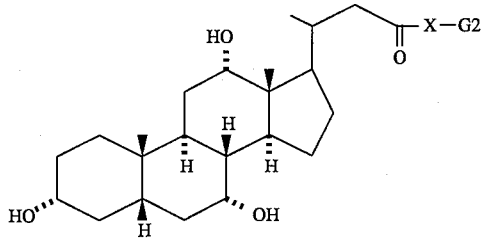
| Ex. | −X−G2 | MS (FAB, 3-NBA/LiCl) |
|---|---|---|
| 15 | 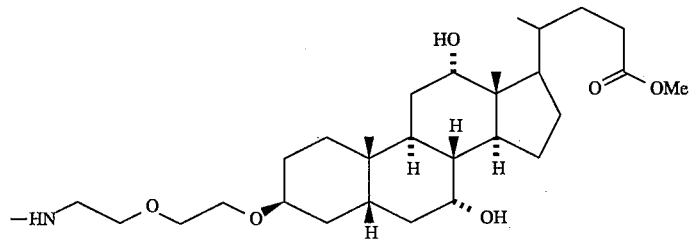 | $C_{52}H_{87}NO_{10}$ (886), 893 (M+Li$^+$) |
| 16 | 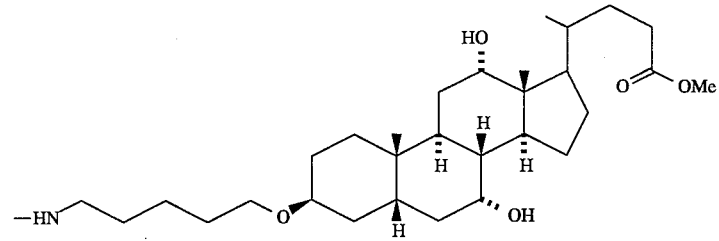 | $C_{54}H_{91}NO_9$ (898), 905 (M+Li$^+$) |
| 17 | 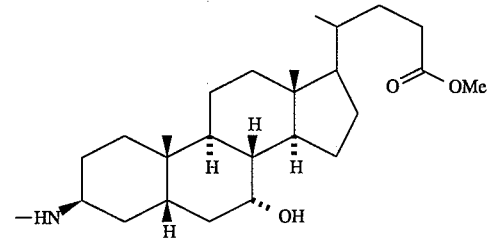 | $C_{48}H_{79}NO_7$ (782), 789 (M+Li$^+$) |
| 18 | 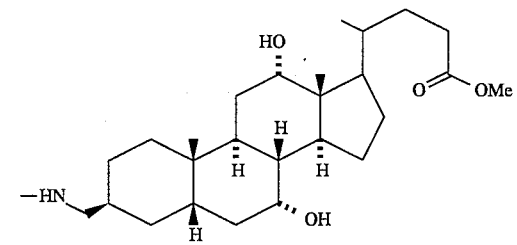 | $C_{49}H_{81}NO_8$ (812), 819 (M+Li$^+$) |
| 19 | 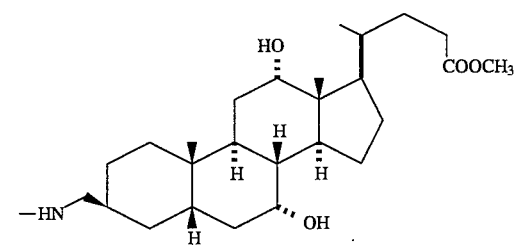 | $C_{55}H_{97}NO_9Si_2$ (972), 979 (M+Li$^+$) |

TABLE 2

[Structure: steroid core with 3α-OH, 7α-OH, 12α-OH, and side chain terminating in C(=O)–X–G2]

| Ex. | –X–G2 | MS (FAB, 3-NBA/LiCl) |
|---|---|---|
| 20 | [Structure: –HN– linked to steroid with 3β-amino, 7α-OH, 12α-OH, side chain CO-OMe] | $C_{47}H_{77}NO_8$ (784), 791 (M+Li$^+$) |
| 21 | [Structure: –HN–CH$_2$CH$_2$–O– linked to steroid 3β-position, 7α-OH, 12α-OH, side chain CO-OMe] | $C_{49}H_{81}NO_9$ (828), 835 (M+Li$^+$) |
| 22 | [Structure: –HN–CH$_2$CH$_2$–O–CH$_2$CH$_2$–O– linked to steroid 3β-position, 7α-OH, 12α-OH, side chain CO-OMe] | $C_{51}H_{85}NO_{10}$ (872), 879 (M+Li$^+$) |
| 23 | [Structure: –HN–(CH$_2$)$_5$–O– linked to steroid 3β-position, 7α-OH, 12α-OH, side chain CO-OMe] | $C_{53}H_{89}NO_9$ (884), 891 (M+Li$^+$) |
| 24 | [Structure: –HN– linked directly to steroid 3β-position, 7α-OH, side chain CO-OMe] | $C_{47}H_{77}NO_7$ (768), 775 (M+Li$^+$) |

TABLE 2-continued
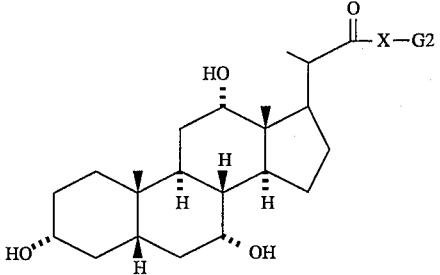
| Ex. | −X−G2 | MS (FAB, 3-NBA/LiCl) |
|---|---|---|
| 25 | 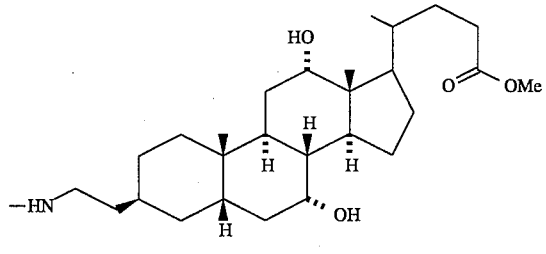 | $C_{49}H_{81}NO_8$ (812), 819 (M+Li$^+$) |
| 26 | | $C_{48}H_{79}NO_9$ (814), 821 (M+Li$^+$) |
TABLE 3
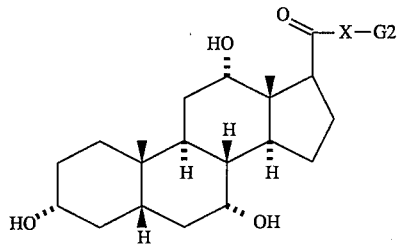
| Ex. | −X−G2 | MS (FAB, 3-NBA/LiCl) |
|---|---|---|
| 27 | | $C_{45}H_{73}NO_8$ (756), 763 (M+Li$^+$) |

TABLE 3-continued
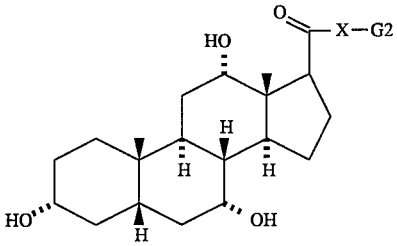
| Ex. | —X—G2 | MS (FAB, 3-NBA/LiCl) |
|---|---|---|
| 28 | 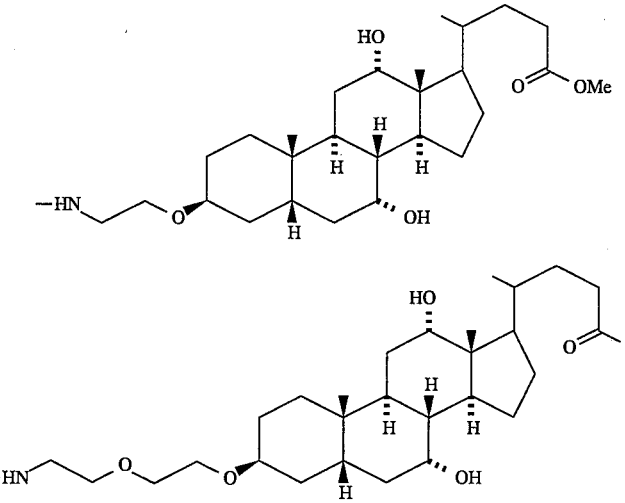 | $C_{47}H_{77}NO_9$ (800), 807 (M+Li$^+$) |
| 29 | 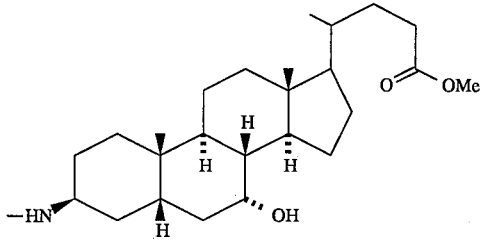 | $C_{49}H_{81}NO_{10}$ (844), 851 (M+Li$^+$) |
| 30 | 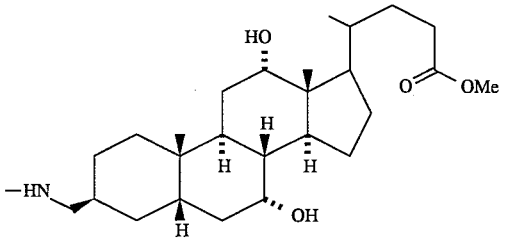 | $C_{45}H_{73}NO_7$ (740), 747 (M+Li$^+$) |
| 31 | | $C_{46}H_{75}NO_7$ (754), 761 (M+Li$^+$) |

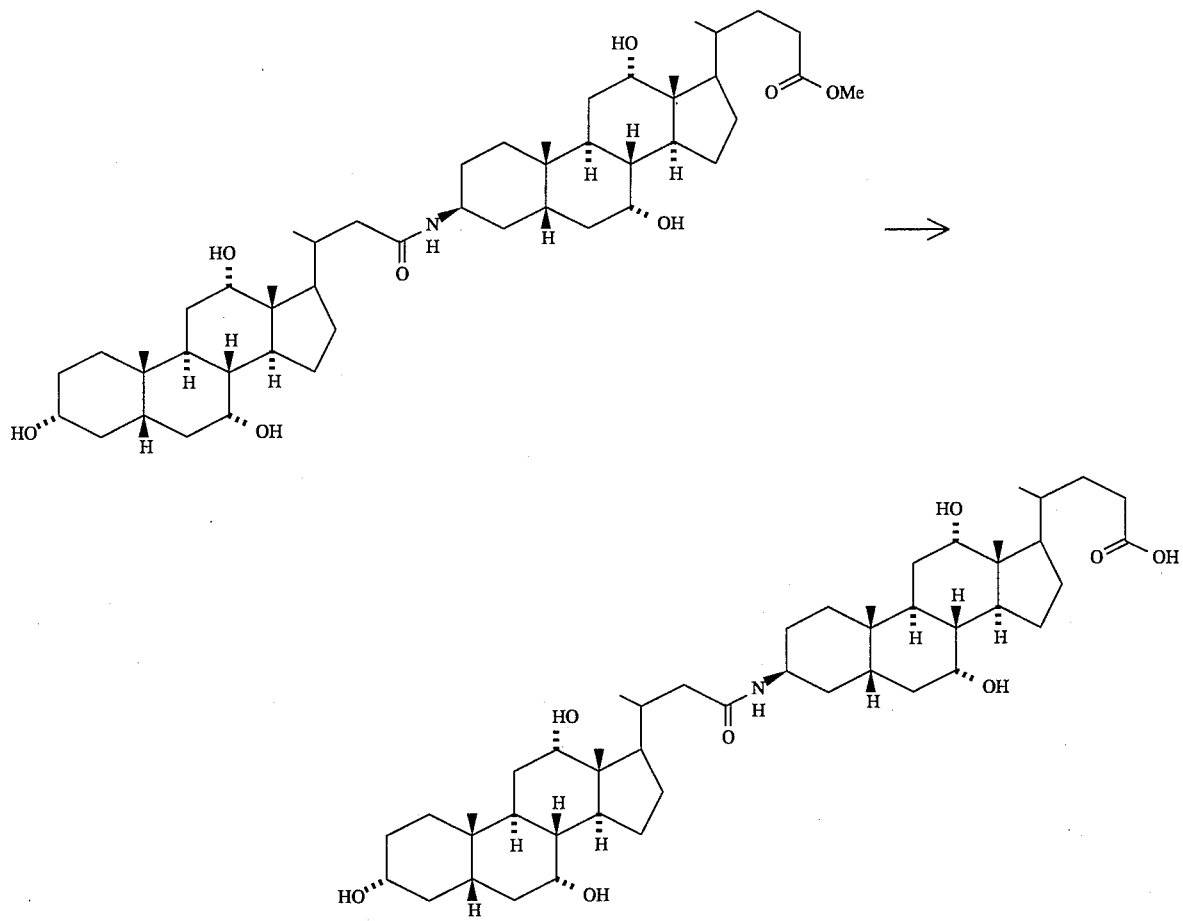

3.0 g (3.76mmol) of Example 13 are dissolved in 80 ml of ethanol, 30 mol of 1N aqueous NaOH are added and the mixture is stirred at room temperature for 16 hours. For working up, 30 ml of water are added and the alcohol is stripped off completely. After acidification with 1N HCl, the precipitate is filtered off with suction, washed with water and dried in vacuo. 2.5 g (85%) of Example 32 are obtained.

MS (FAB, 3-NBA/LiCl) $C_{47}H_{77}NO_8$ (784), 791 (M+Li$^+$)

Examples 33 to 50 of Tables 4 to 6 are obtained analogously to Example 32 from the methyl esters (Tables 1–3).

TABLE 4

[Structure: steroid nucleus with HO at 12-position, HO at 3-position, OH at 7-position, and side chain terminating in —C(=O)—X—G2]

| Ex. | —X—G2 | MS (FAB, 3-NBA/LiCl) |
|---|---|---|
| 33 | [structure with —HN—CH₂CH₂—O— linked to bile acid derivative with HO, OH, and COOH groups] | C₄₉H₈₁NO₉ (828), 835 (M+Li⁺) |
| 34 | [structure with —HN—CH₂CH₂—O—CH₂CH₂—O— linked to bile acid derivative] | C₅₁H₈₅NO₁₀ (872), 879 (M+Li⁺) |
| 35 | [structure with —HN—(CH₂)₅—O— linked to bile acid derivative] | C₅₃H₈₈NO₉ (884), 891 (M+Li⁺) |
| 36 | [structure with —HN— directly linked to bile acid derivative] | C₄₇H₇₇NO₇ (768), 775 (M+Li⁺) |
| 37 | [structure with —HN—CH₂— linked to bile acid derivative] | C₄₈H₇₉NO₈ (798), 805 (M+Li⁺) |

TABLE 4-continued
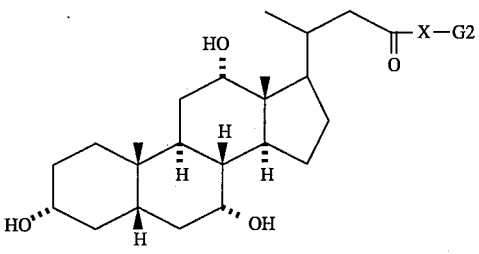
| Ex. | —X—G2 | MS (FAB, 3-NBA/LiCl) |
|---|---|---|
| 38 | 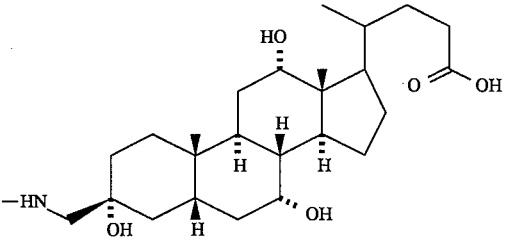 | $C_{48}H_{79}NO_9$ (814), 821 (M+Li$^+$) |
TABLE 5
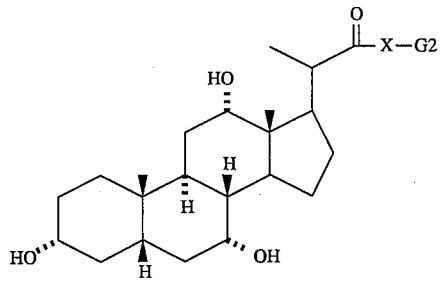
| Ex. | —X—G2 | MS (FAB, 3-NBA/LiCl) |
|---|---|---|
| 39 | 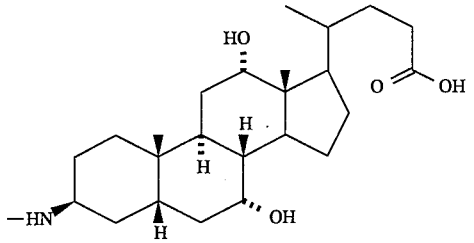 | $C_{46}H_{75}NO_8$ (770), 777 (M+Li$^+$) |
| 40 | 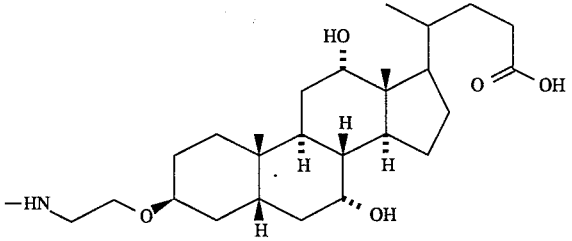 | $C_{48}H_{79}NO_9$ (814), 821 (M+Li$^+$) |

TABLE 5-continued
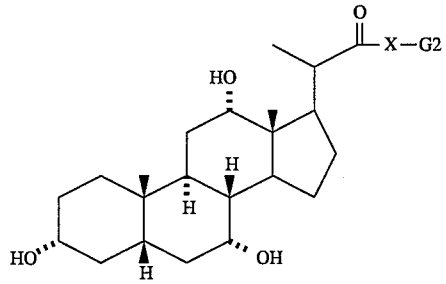
| Ex. | –X–G2 | MS (FAB, 3-NBA/LiCl) |
|---|---|---|
| 41 | 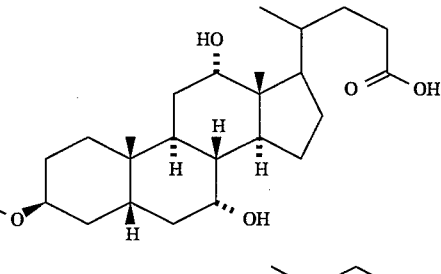 | $C_{50}H_{83}NO_{10}$ (858), 865 (M+Li$^+$) |
| 42 | 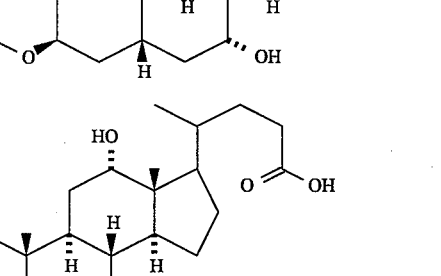 | $C_{52}H_{87}NO_9$ (870), 877 (M+Li$^+$) |
| 43 | 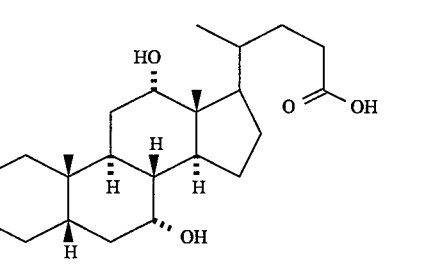 | $C_{46}H_{75}NO_7$ (754), 755 (M+Li$^+$) |
| 44 | 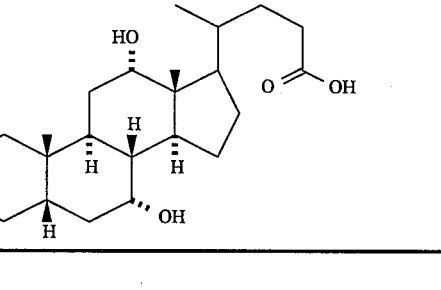 | $C_{48}H_{79}NO_8$ (798), 805 (M+Li$^+$) |
| 45 | | $C_{47}H_{77}NO_9$ (800), 807 (M+Li$^+$) |

TABLE 6

[Structure: steroid core with HO (12α), HO (3α), OH (7α), and carboxylic acid C(=O)-X-G2 at position 17]

| Ex. | -X-G2 | MS (FAB, 3-NBA/LiCl) |
|---|---|---|
| 46 | [structure with -HN- linked to second steroid bearing HO, OH groups and carboxylic acid side chain] | $C_{44}H_{71}NO_8$ (742), 749 (M+Li$^+$) |
| 47 | [structure with -HN-CH$_2$CH$_2$-O- linked to second steroid] | $C_{46}H_{75}NO_9$ (786), 793 (M+Li$^+$) |
| 48 | [structure with -HN-CH$_2$CH$_2$-O-CH$_2$CH$_2$-O- linked to second steroid] | $C_{48}H_{79}NO_{10}$ (830), 837 (M+Li$^+$) |
| 49 | [structure with -HN- linked to second steroid (7β-OH)] | $C_{44}H_{71}NO_7$ (726), 733 (M+Li$^+$) |
| 50 | [structure with -HN-CH$_2$- linked to second steroid] | $C_{45}H_{73}NO_7$ (740), 747 (M+Li$^+$) |

Examples 51 to 54 from Table 7 are obtained analogously to Example 5 from the acids described above.

TABLE 7
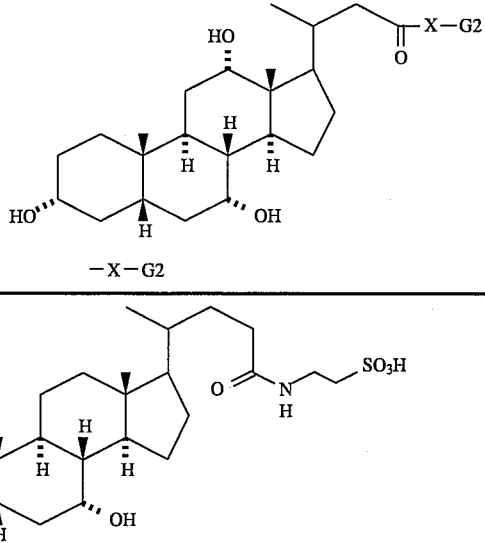
| Ex. | -X-G2 | MS (FAB, 3-NBA/LiCl) |
|---|---|---|
| 51 | 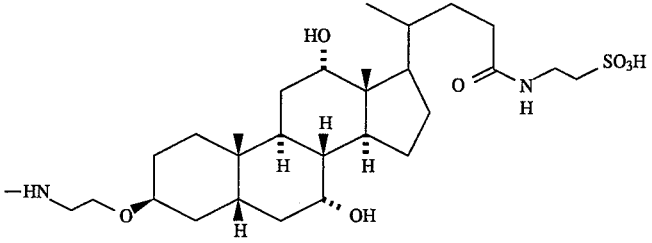 | $C_{49}H_{82}N_2O_{10}S$ (891), 892 (M+H$^+$) |
| 52 | 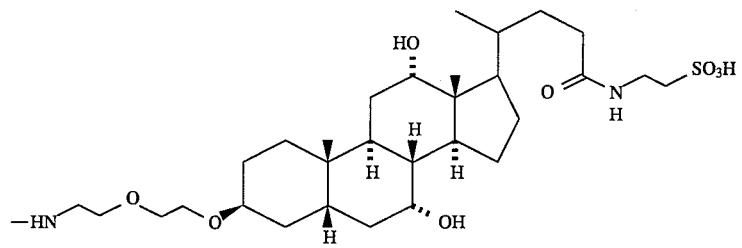 | $C_{51}H_{86}N_2O_{11}S$ (935), 942 (M+H$^+$) |
| 53 | 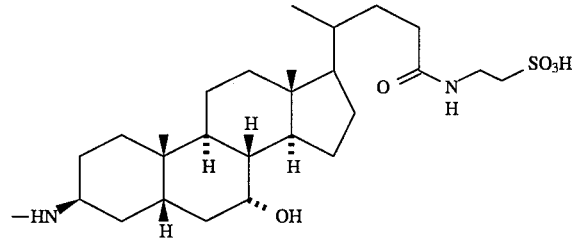 | $C_{53}H_{90}N_2O_{12}S$ (976), 1024 (M+H$^+$) |
| 54 | | $C_{49}H_{82}N_2O_9S$ (875), 920 (M+H$^+$) |
Examples 55 to 57 of Table 8 are obtained analogously to Example 4.

TABLE 8
| | | |
|---|---|---|
| Ex. | −X−G2 | MS (FAB, 3-NBA/LiCl) |
| 55 | 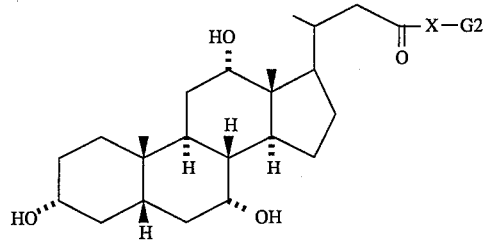 | $C_{49}H_{80}N_2O_9$ (841), 842 (M+H⁺) |
| 56 | 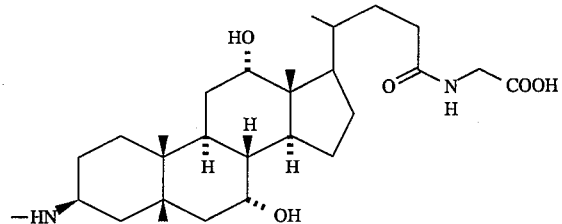 | $C_{51}H_{84}N_2O_{10}$ (885), 892 (M+Li⁺) |
| 57 | 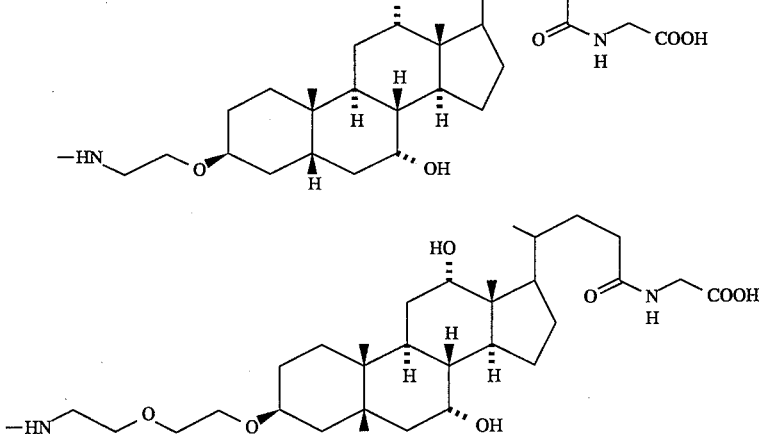 | $C_{53}H_{88}N_2O_{11}$ (929), 936 (M+Li⁺) |
Examples 58 to 63 of Table 9 are obtained analogously to Example 13.

TABLE 9

[Structure: steroid core with G1-NH at C3, OH at C7, OH at C12, and -CH(CH3)CH2C(=O)OMe side chain]

(in the following formulae, the free valency of G1 is not shown).

| Ex. | G1— | MS (FAB, 3-NBA/LiCl) |
|---|---|---|
| 58 | [steroid with HO at C3, OH at C7, HO at C12, aldehyde side chain] | $C_{48}H_{79}NO_8$ (798), 805 (M+Li$^+$) |
| 59 | [steroid with HO at C3, OH at C7, aldehyde side chain] | $C_{48}H_{79}NO_7$ (782), 789 (M+Li$^+$) |
| 60 | [steroid with HO at C3, OH at C7 (β), aldehyde side chain] | $C_{48}H_{79}NO_8$ (782), 789 (M+Li$^+$) |
| 61 | [steroid with HO at C3, OH at C7, HO at C12 (α), aldehyde side chain] | $C_{48}H_{79}NO_8$ (798), 805 (M+Li$^+$) |
| 62 | [steroid with HO at C3, OH at C7, HO at C12, aldehyde side chain] | $C_{47}H_{77}NO_8$ (784), 791 (M+Li$^+$) |

TABLE 9-continued
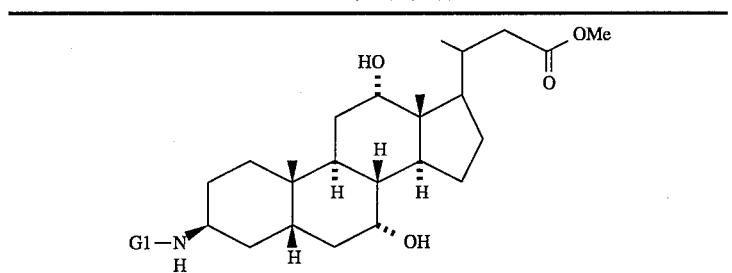
(in the following formulae, the free valency of G1 is not shown).
| Ex. | G1— | | MS (FAB, 3-NBA/LiCl) |
|---|---|---|---|
| 63 | | O<br>∥ | $C_{46}H_{75}NO_8$ (770),<br>777 (M+Li$^+$) |
Examples 64 to 69 of Table 10 are obtained analogously to Example 32.
TABLE 10
(The free valency of G1 is not shown in the following formulae)
| Ex. | G1— | MS (FAB, 3-NBA/LiCl) |
|---|---|---|
| 64 | | $C_{47}H_{77}NO_8$ (784),<br>791 (M+Li$^+$) |
| 65 | | $C_{47}H_{77}NO_7$ (768),<br>775 (M+Li$^+$) |

TABLE 10-continued (The free valency of G1 is not shown in the following formulae)

| Ex. | G1— | MS (FAB, 3-NBA/LiCl) |
|---|---|---|
| 66 | | $C_{47}H_{77}NO_7$ (768), 775 (M+Li$^+$) |
| 67 | | $C_{47}H_{77}NO_8$ (784), 791 (M+Li$^+$) |
| 68 | | $C_{46}H_{75}NO_8$ (770), 771 (M+Li$^+$) |
| 69 | | $C_{45}H_{73}NO_8$ (756), 763 (M+Li$^+$) |

The sodium salts of Example 32 and all the examples of Tables 4 to 8 and 10 can be prepared. The compound is dissolved in methanol, an equimolar amount of 1N aqueous NaOH is added and the mixture is then evaporated in vacuo.

Table 11 shows measurement values for the inhibition of [$^3$H]-taurocholate uptake in the brush border membrane vesicles of the ileum of rabbits. The quotients of the IC$_{50}$ and IC$_{50Na}$ values of the reference substance as taurochenodeoxycholate (TCDC) and the particular test substance are stated.

TABLE 11

| Compounds from Example | $\dfrac{IC_{50}\text{-TCDC [}\mu\text{mol]}}{IC_{50}\text{-substance [}\mu\text{mol]}}$ | $\dfrac{IC_{50Na}\text{-TCDC [}\mu\text{mol]}}{IC_{50Na}\text{-substance [}\mu\text{mol]}}$ |
|---|---|---|
| 32 | 0.76 | 0.65 |
| 35 | 1.00 | 0.91 |
| 36 | 0.78 | 1.14 |
| 41 | 0.55 | 0.58 |

TABLE 11-continued

| Compounds from Example | IC$_{50}$-TCDC [μmol] / IC$_{50}$-substance [μmol] | IC$_{50Na}$-TCDC [μmol] / IC$_{50Na}$-substance [μmol] |
| --- | --- | --- |
| 43 | 0.69 | 0.78 |
| 57 | 0.34 | 0.34 |
| 65 | 0.85 | 0.64 |
| 69 | 0.78 | 0.86 |

We claim:

1. A bile acid derivative of the formula I

wherein $G_1$ is linked via the side chain on atom No. 17 with the bonding member X to atom No. 3 of $G_2$, and $G_1$ is a radical of the formula II

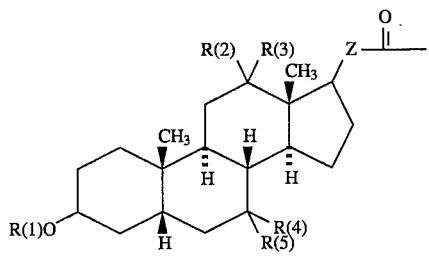

in which

Z is one of the following radicals

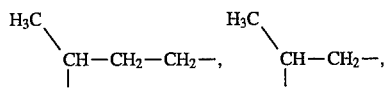

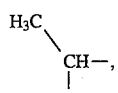

or a single bond,

R(1) is H, an alkyl radical having 1 to 10 carbon atoms or an alkenyl radical having 2 to 10 carbon atoms, R(2), R(3), R(4), R(5) are independently H, OH or R(2) and R(3), or R(4) and R(5) together form the oxygen of a carbonyl group, X is a single bond or a bridge member of the formula III

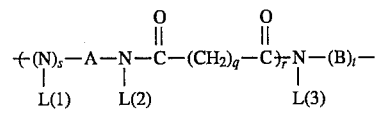

in which

A is an alkylene chain, which is branched or unbranched, and which is optionally interrupted by —O—, —S—, or phenylene, the linkage of the phenyl ring being in the ortho-, meta- or para-position and the chain comprising 2 to 12 chain members, B is an alkylene chain which is branched or unbranched, and which is optionally interrupted by —O—, —S—, or phenylene, the linkage of the phenyl ring being in the ortho-, meta- or para-position and the chain comprising 2 to 12 chain members, L(1), L(2) and L(3) are identical or different and are selected from H, an alkyl radical or alkenyl radical having up to 10 carbon atoms, a cycloalkyl radical having 3 to 8 carbon atoms, a phenyl radical, which is unsubstituted or mono- to trisubstituted by F, Cl, Br, ($C_1$–$C_4$-alkyl or ($C_1$–$C_4$)-alkoxy, or a benzyl radical, which is unsubstituted or mono- to trisubstituted by F, Cl, Br, ($C_1$–$C_4$)-alkyl or ($C_1$–$C_4$)-alkoxy, q is 0 to 5;

r is 0 or 1;

s is 0 or 1; and t is 0 or 1, $G_2$ is a radical of the formula IV

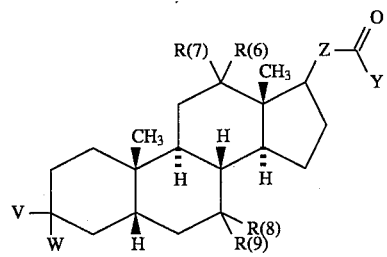

in which Z is one of the following radicals

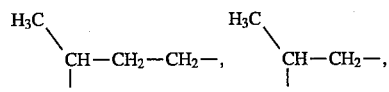

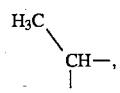

or a single bond, with the proviso that Z may be

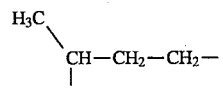

in only one of formulas II and IV;

V is —O— or

when

W is H or,

V is —CH$_2$— or —CH$_2$—CH$_2$— when W is H or OH,

Y is —OL, NHL,

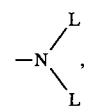

or an amino acid or amino-sulfonic acid bonded via the amino group, selected from the group consisting of —NH—CH$_2$—COOH, —NH—CH$_2$—CH$_2$—, SO$_3$H,

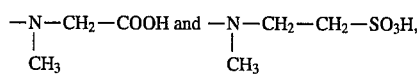

in which L is H, an alkyl radical or alkenyl radical having up to 10 carbon atoms, a cycloalkyl radical having 3 to 8 carbon atoms, a phenyl radical, which is unsubstituted or mono- to trisubstituted by F, Cl, Br, $(C_1-C_4)$-alkyl or $(C_1-C_4)$-alkoxy, or a benzyl radical, which is unsubstituted or mono- to trisubstituted by F, Cl, Br, $(C_1-C_4)$-alkyl or $(C_1-C_4)$-alkoxy, and R(6), R(7), R(8), R(9) are independently H, OH or R(6) and R(7) or R(8) and R(9) together form the oxygen of a carbonyl group.

2. The bile acid derivative of the formula I, as claimed in claim 1, wherein L is an alkenyl radical having 2 to 10 carbon atoms.

3. The bile acid derivative of formula I, as claimed in claim 1, wherein one or more of L(1), L(2) or L(3) is an alkenyl radical having 2 to 10 carbon atoms.

4. A medicament comprising a pharmaceutically effective amount of a bile acid derivative as claimed in claim 1 and a pharmaceutically acceptable carrier.

5. A method of treating a host in need of a hypolipodemic agent comprising administering an effective amount of a bile acid derivative as claimed in claim 1.

* * * * *

UNITED STATES PATENT AND TRADEMARK OFFICE
CERTIFICATE OF CORRECTION

PATENT NO. : 5,512,558
DATED : April 30, 1996
INVENTOR(S) : Alfons ENHSEN et al.

It is certified that error appears in the above-indentified patent and that said Letters Patent is hereby corrected as shown below:

Title page, item [57], In the Abstract, line 2 "medicaments nor-Bile" should read --medicaments. nor-Bile--.

Claim 1, column 53, line 47, after "R(3)", delete ",".

Claim 1, column 54, line 6, "$(C_1-C_4$-alkyl" should read --$(C_1-C_4)$-alkyl--.

Claim 1, column 54, line 6, "$(C_1-C_4$-alkoxy" should read --$(C_1-C_4)$-alkoxy--.

Signed and Sealed this

Twelfth Day of August, 1997

Attest:

BRUCE LEHMAN

*Attesting Officer*    *Commissioner of Patents and Trademarks*